(12) United States Patent
Bell et al.

(10) Patent No.: US 9,328,126 B2
(45) Date of Patent: May 3, 2016

(54) NORBORNENYLHYDROCARBYLENE DIHYDROCARBYLBORANES AND METHODS OF MAKING THE SAME

(71) Applicant: PROMERUS, LLC, Brecksville, OH (US)

(72) Inventors: Andrew Bell, Brecksville, OH (US); Keitaro Seto, Brecksville, OH (US); Stephen Westcott, Sackville (CA); Robert G Potter, Brecksville, OH (US)

(73) Assignee: PROMERUS, LLC, Brecksville, OH (US)

( * ) Notice: Subject to any disclaimer, the term of this patent is extended or adjusted under 35 U.S.C. 154(b) by 0 days.

(21) Appl. No.: 14/759,063

(22) PCT Filed: Jan. 31, 2014

(86) PCT No.: PCT/US2014/014026

§ 371 (c)(1),
(2) Date: Jul. 2, 2015

(87) PCT Pub. No.: WO2014/121008

PCT Pub. Date: Aug. 7, 2014

(65) Prior Publication Data

US 2015/0353582 A1    Dec. 10, 2015

Related U.S. Application Data

(60) Provisional application No. 61/758,938, filed on Jan. 31, 2013.

(51) Int. Cl.
| | | |
|---|---|---|
| *C07F 5/02* | (2006.01) | |
| *C07C 41/03* | (2006.01) | |
| *C07C 51/15* | (2006.01) | |
| *C07C 29/03* | (2006.01) | |
| *C07C 303/28* | (2006.01) | |
| *C07C 17/093* | (2006.01) | |
| *C07C 17/361* | (2006.01) | |

(52) U.S. Cl.
CPC ............. *C07F 5/027* (2013.01); *C07C 17/093* (2013.01); *C07C 17/361* (2013.01); *C07C 29/03* (2013.01);

(Continued)

(58) Field of Classification Search
None
See application file for complete search history.

(56) References Cited

U.S. PATENT DOCUMENTS 3,254,129 A * 5/1966 Brown ................. C07C 29/54
528/394
4,713,380 A * 12/1987 Brown ................. C07C 29/48
568/1

(Continued)

OTHER PUBLICATIONS

Yoshiharu Inou, Useful Synthetic Routes to Pure exo-5-Vinyl-2-norbornene and endo-5-Vinyl-2-norbornene, Bulletin Chemical Society of Japan, vol. 60, No. 5, pp. 1954-1956 (1987).

(Continued)

*Primary Examiner* — Rosalynd Keys
(74) *Attorney, Agent, or Firm* — Balaram Gupta

(57) ABSTRACT

Embodiments of norbornenylhydrocarbylene dihydrocarbylboranes represented by the Formula (I),

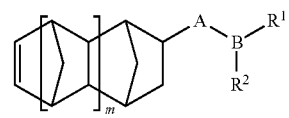

and methods of forming such norbornenylhydrocarbylene dihydrocarbylboranes are provided, where m is 0, 1 or 2, A is a $C_2$ to $C_{12}$ hydrocarbylene group; $R^1$ and $R^2$ are independently selected from a substituted or unsubstituted $C_1$ to $C_{12}$ hydrocarbyl, substituted or unsubstituted, monocyclic or bicyclic $C_5$ to $C_7$ rings, and $R^1$ and $R^2$, taken together with the boron atom to which they are attached, can form a monocyclic or bicyclic ring; wherein the norbornenylhydrocarbylene dihydrocarbylboranes of Formula (I) are subject to the proviso that 9-norbornenylethyl-9-borabicyclo[3.3.1]nonane is not included.

21 Claims, 2 Drawing Sheets

(52) U.S. Cl.
CPC ............... *C07C 41/03* (2013.01); *C07C 51/15* (2013.01); *C07C 303/28* (2013.01); *C07C 2102/42* (2013.01)

(56) References Cited

U.S. PATENT DOCUMENTS 5,093,433 A * 3/1992 Chung .................... C08F 8/00
　　　　　　　　　　　　　　　　　　　525/332.1

5,122,490 A　　6/1992　Uwai et al.

OTHER PUBLICATIONS

Alexey V. Kalinin, et al., Di(isopropylprenyl)borane: A New Hydroboration Reagent for the Synthesis of Alkyl and Alkenyl Boronic Acids, Agnew. Chem. Int. Ed., vol. 42, No. 29, pp. 3399-3404 (2003).

* cited by examiner

NORBORNENYLHYDROCARBYLENE DIHYDROCARBYLBORANES AND METHODS OF MAKING THE SAME

CROSS REFERENCE TO RELATED APPLICATIONS

This application is a national phase application of PCT Application No. PCT/US2014/014026, filed Jan. 31, 2014, and published as International Publication No. WO 2014/121008 A1 on Aug. 7, 2014, and which claims the benefit of U.S. Provisional Application No. 61/758,938, filed Jan. 31, 2013, each of which is incorporated herein by reference in its entirety.

TECHNICAL FIELD

Embodiments of the present invention relate to norbornenylhydrocarbylene dihydrocarbylboranes, methods for selectively making such dihydrocarbylboranes and derivative products made therefrom.

In U.S. Patent Application Publication No. US 2009/0054714 ("the '714 publication"), it is recognized that the exo-isomer of vinylnorbornene (VNB), as well as the exo-isomers of other alkenylnorbornenes, are promising "building blocks" in the synthesis of various biologically active compounds that exhibit diverse physiological activity. In addition, the '714 publication discloses that the exo- and endo-isomers of such alkenylnorbornenes exhibit different reactivity when employed as monomers in polymerization processes and that the use of one or the other isomer can provide polymers with different chemical and/or physical properties.

While the '714 publication provides a useful pathway to isolating essentially pure isomers of alkenylnorbornenes, the publication does not address conversion of the pendent alkenyl group that would be necessary for synthesis of said various biologically active compounds or monomers.

As is well known to those of ordinary skill in the chemical arts, hydroboration is a powerful tool in synthetic organic chemistry; for example, it can be used in the formation of a reactive intermediate that may serve as a first step in a process for preparing a wide range of second and third generation products. For example, in addition to the hydrolysis of a hydroborated intermediate to an alcohol such as in Inoue, as discussed below, alternative synthetic pathways to second and third generation products include, but are not limited to, protonolysis, halogenolysis, oxidation to aldehydes and carboxylic acids, sulfuridation, animation, cyanidation and bond forming reactions such as alkylation and arylation.

It is further well known that hydroboration is generally characterized by the syn-addition of the hydroboration agent to the alkene or alkyne reagent, the boron atom of the hydroboration agent adding to the least hindered carbon of the alkene or alkyne reagent, and thus generally provides highly regiostereochemical selectivity. Further still, where the boron atom of the hydroboration agent is substituted with sterically demanding substituents, the regiostereochemical selectivity of the addition of the hydroboration agent across the unsaturated bond of the alkene or alkyne reagent is generally enhanced. For example, as reported in Table 6.1 (reproduced below) of Hydroboration and Organic Synthesis 9-Borabicyclo[3.3.1]nonane (9-BBN) (ISBN: 978-3-540-49075-3), where 1-hexene is hydroborated and then oxidized to an alcohol, the regiostereochemical selectivity of the hydroboration agent (as measured by the product distribution) increases as does its steric hindrance or bulk.

| Olefin | Hydroboration agent | Product distribution (%) | |
|--------|---------------------|---------|---------|
|        |                     | 1-ol    | 2-ol    |
| 1-Hexene | $BH_3$ | 94 | 6 |
|        | $Sia_2BH$ | 99 | 1 |
|        | 9-BBN | >99.9 | | borane ($BH_3$),
disiamylborane ($Sia_2BH$),
9-boracyclo[3.3.1]nonane (9-BBN)

Thus it would seem that, of the three hydroboration agents listed in the table above, 9-BBN would be the most advantageous for making the aforementioned "building blocks" since it exhibits the highest regiostereochemical selectivity.

However, when alkenylnorbornenes are used as reagents instead of 1-hexene, the regiostereochemical selectivity of 9-BBN may be more complex. For example, Y. Inoue, in *Bull. Chem. Soc. Jpn.* Vol. 60, 1954-1956 (1987), reported that hydroboration of endo-/exo-vinylnorbornene with 9-BBN and followed by oxidation resulted in the formation of endo-/exo-NBEtOH (2) in about 70% yield, together with a 6% yield of a mixture of 6-vinyl-2-norbornanol (3) and 5-vinyl-2-norbornanol (4) and a 4% yield of a mixture of 6-(2-hydroxyethyl)-2-norbornanol (5) and 5-(2-hydroxyethyl)-2-norbornanol (6), as shown below:

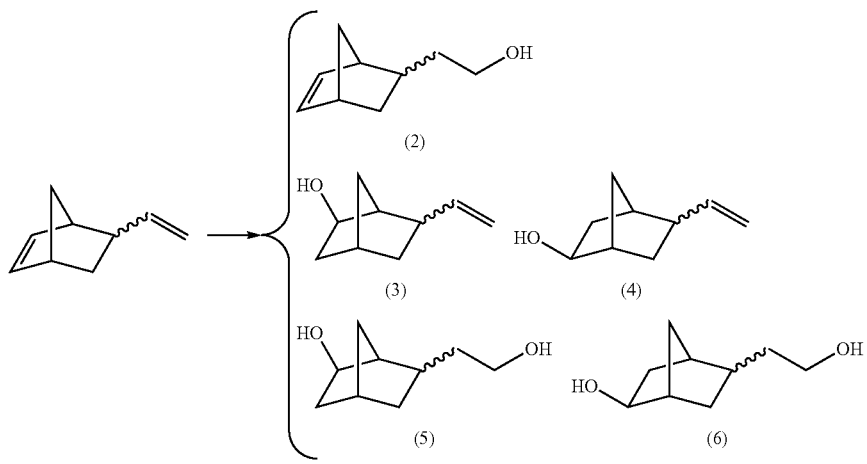

As is seen from the reaction products produced and the yields thereof, selectivity of the addition to the vinyl double bond, as evidenced by the formation of only the terminal alcohols of (2), (5) and (6) is in accordance with the selectivity of the regiostereochemistry reported for the hydroboration of 1-hexene. However, the yield of the product mixtures resulting from addition across the norbornene double bond, as evidenced by the formation of product groups "(3)/(4)" and "(5)/(6)" provide a very different result. As reported, an essentially equal amount of each product group is formed where for the (3)/(4) group addition is to only the norbornene double bond and for the (5)/(6) group, addition is to both double bonds. Thus, where selective addition of a hydroboration agent to the vinylic or alkenyl double bond of vinyl or alkenylnorbornenes is desired, e.g., as in product (2) above, 9-BBN is reported by Inoue to be only marginally selective (70.7% yield) to the vinylic bond, making hydroboration of alkenylnorbornenes with 9-BBN a less than desirable synthetic pathway to selectively obtaining high yields of norbornenylhydrocarbylene dihydrocarbylboranes and/or second and third generation products thereof. Therefore, providing hydroboration agents, other than 9-BBN, that can exhibit higher or enhanced regiostereochemical selectivity for an alkenyl unsaturation as opposed to a norbornene unsaturation would be desirable.

DETAILED DESCRIPTION

Figure 1:
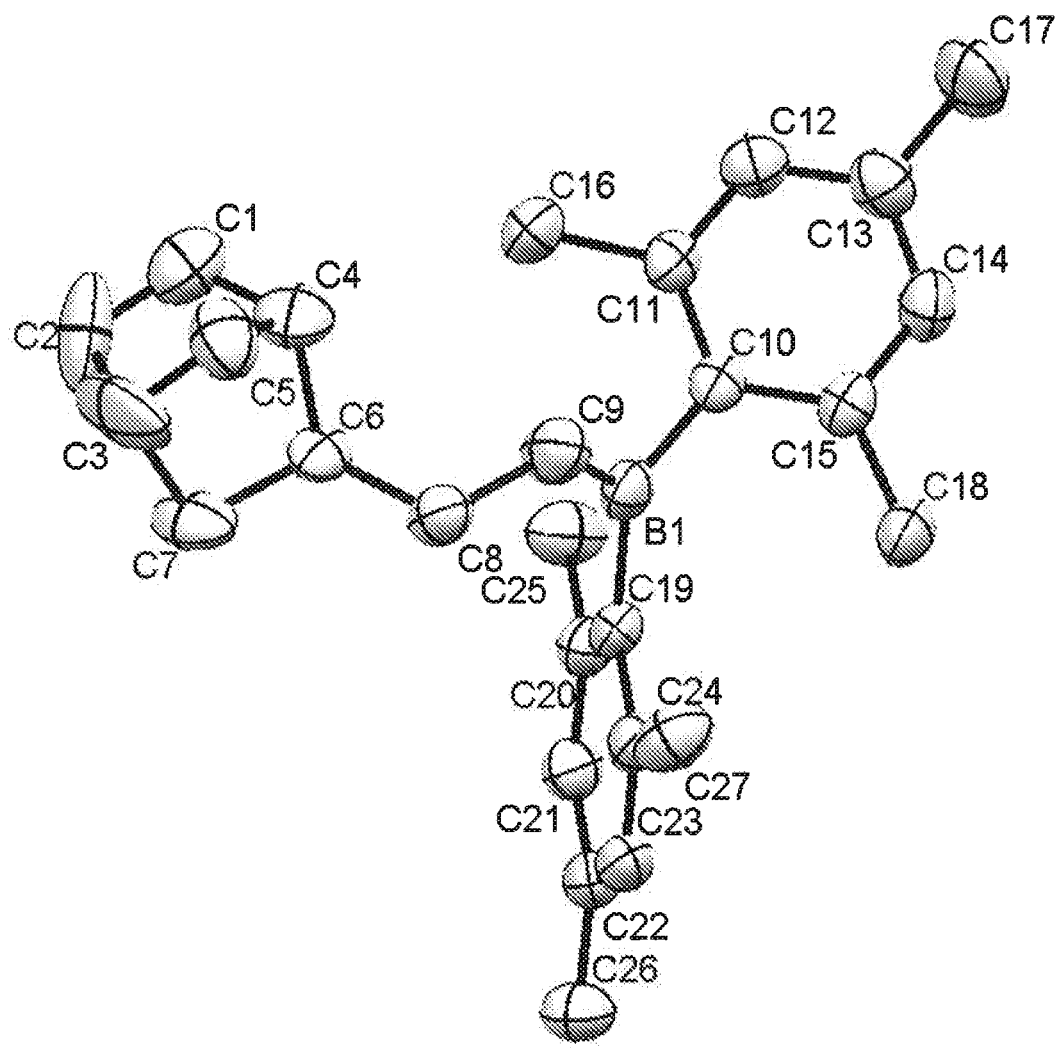
FIG. 1 shows an Oak Ridge Thermal Ellipsoid Plot (ORTEP) diagram of exo-NBCH$_2$CH$_2$B(mesityl)$_2$, a trihydrocarbylborane embodiment in accordance with the present invention.

Embodiments in accordance with the present invention encompass norbornene-type monomers that are the result of the hydroboration of alkenylnorbornene reagents with hydroboration agents having enhanced regiostereochemical selectivity, as well as norbornene-type monomers having at least one of an alkyl, an alcohol, an ether, an alkaryl, a carboxylic acid, a sulfonic acid ester or an alkyl halide pendent group derived from such resultant norbornene-type monomers. Where the aforementioned hydroboration agents are referred to as having enhanced regiostereochemical selectivity, it will be understood to mean that the hydroboration agents react at the alkenyl unsaturation of an alkenylnorbornene reagent and react in yields of at least 85% to form products that have at least 90%, regiostereochemistry at the least hindered carbon atom of the alkenyl unsaturation. It will further be understood that some such embodiments encompass hydroborating only the alkenyl unsaturation of an alkenylnorbornene reagent in yields of at least 95% and, in some others, hydroborating only the alkenyl unsaturation of an alkenylnorbornene reagents in yields of at least 99%. As used herein the terms, "regiostereochemical selective" or "regioselective" mean the same and can be used interchangeably, and means selective addition of organoborane to the terminal alkenyl double bond.

Accordingly, some embodiments of the present invention encompass the generation of hydroboration agents, other than 9-BBN, that can provide the aforementioned enhanced regiostereochemical selectivity and thus form desired norbornenylhydrocarbylene dihydrocarbylboranes. Additionally, some embodiments in accordance with the present invention encompass the norbornenylhydrocarbylene dihydrocarbylboranes so formed as well as their use as "building blocks" for the generation of a variety of functionalized norbornene monomers having a specific regiostereochemical configuration which has been previously been difficult or even impossible to make by other methods in the high yields exhibited by embodiments of the present invention.

As used herein, the articles "a," "an," and "the" include plural referents unless otherwise expressly and unequivocally limited to one referent.

Since all numbers, values and/or expressions referring to quantities of ingredients, reaction conditions, etc., used herein and in the Exhibits and Claims appended hereto, are subject to the various uncertainties of measurement encountered in obtaining such values, unless otherwise indicated, all are to be understood as modified in all instances by the term "about."

Where a numerical range is disclosed herein, unless otherwise specified, such range is continuous, inclusive of both the minimum and maximum values of the range as well as every value between such minimum and maximum values. Still further, where a range refers to integers, only the integers from the minimum value to and including the maximum value of such range are included. In addition, where multiple ranges are provided to describe a feature or characteristic, such ranges can be combined. That is to say that, unless otherwise indicated, all ranges disclosed herein are to be understood to encompass any and all subranges subsumed therein. For example, a stated range of from "1 to 10" should be considered to include any and all subranges between the minimum value of 1 and the maximum value of 10. Exemplary subranges of the range 1 to 10 include, but are not limited to, 1 to 6.1, 3.5 to 7.8, and 5.5 to 10, and so on. Further, where an integer range of from "0 to 12" is provided, it will also be considered to include any and all subranges as described above.

As defined herein, the terms "norbornene-type," "polycycloolefin" and "poly(cyclic) olefin" can be used interchangeably to refer to addition polymerizable monomers that encompass at least one norbornene structure, bicyclo[2.2.1] hept-2-ene, such as shown below:

Additionally, the term norbornene-type monomer can be used to refer to any substituted norbornene(s), or substituted and unsubstituted higher cyclic derivatives thereof. The formula, shown below, is representative of such norbornene-type monomers:

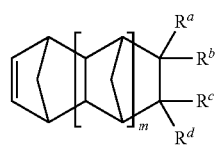

where m is 0, 1 or 2 and each occurrence of $R^a$, $R^b$, $R^c$ and $R^d$ independently represents hydrogen, a hydrocarbyl or other substituent.

As used herein, "hydrocarbyl" refers to a monovalent hydrocarbon radical or group that contains only carbon and hydrogen, non-limiting examples being alkyl, cycloalkyl, alkenyl, cycloalkenyl, alkynyl, aryl, aralkyl and alkaryl. As used herein, "hydrocarbylene" refers to a divalent radical formed by removing a hydrogen atom from any aforementioned hydrocarbyl radicals.

As used herein, "halohydrocarbyl" and "halohydrocarbylene" refer to any of the previously described hydrocarbyl and hydrocarbylene groups where at least one hydrogen has been replaced by a halogen, e.g., trifluoromethylene and fluorophenyl. It follows then that the terms "perhalocarbyl" and "perhalocarbylene" refer to a hydrocarbyl or hydrocarbylene group where all hydrogens have been replaced by a halogen, e.g., pentafluorophenyl or tetrafluroethylene.

As used herein, the terms "heterohydrocarbyl" or "heterohydrocarbylene" refer to any of the previously described hydrocarbyl or hydrocarbylene groups where at least one of the carbon atoms is replaced with N, O, S, Si or P. Non-limiting examples include appropriate heterocyclic aromatic groups such as pyrrolyl, furanyl, and pyridinyl as well as appropriate non-aromatic groups such as alcohols, ethers, thioethers and silyl ethers.

Additionally, it will be understood that the terms "hydrocarbyl" or "hydrocarbylene" can be used as generic terms inclusive of any of the more specific terms described above. Furthermore, it will be understood that any such hydrocarbyl or hydrocarbylene radicals can be further substituted. Non-limiting examples of suitable substituent groups include, among others, hydroxyl groups, benzyl groups, carboxylic acid groups, carboxylic acid ester groups, amide groups, and imide groups.

As used herein, the terms "alkyl" or "alkylene" and "cycloalkyl" or "cycloalkylene" refer, respectively, to acyclic or cyclic saturated hydrocarbyls or hydrocarbylenes having an appropriate carbon chain length from $C_1$ to $C_{25}$. Non-limiting examples of suitable alkyl groups include, but are not limited to, $-CH_3$, $-(CH_2)_3CH_3$, $-(CH_2)_4CH_3$, $-(CH_2)_5CH_3$, $-(CH_2)_9CH_3$, $-(CH_2)_{23}CH_3$, cyclopentyl, methylcyclopentyl, cyclohexyl and methylcyclohexyl, as well as their hydrocarbylene analogs.

As used herein, the terms "alkenyl" or "alkenylene" and "cycloalkenyl" or "cycloalkenylene" refer, respectively, to acyclic or cyclic saturated hydrocarbon groups having at least one carbon to carbon double bond and an appropriate carbon chain length of from $C_2$ to $C_{25}$. Non-limiting examples include, among others, vinyl or ethenyl groups and groups derived from propylene, butene, cyclopentane and cyclohexene, as well as their hydrocarbylene analogs.

As used herein, the terms "aryl" and "arylene" refer to aromatic hydrocarbyls that include, without limitation, groups such as phenyl, tolyl, biphenyl, xylyl, naphthalenyl, anthracenyl, as well as their hydrocarbylene analogs.

The terms "alkaryl" or "aralkyl" are used herein interchangeably and refer to an aromatic hydrocarbyl group such as benzyl, phenethyl, phenylbutyl, and phenhexyl.

The norbornenylhydrocarbylene dihydrocarbylborane embodiments disclosed herein include those represented by Formula (I), as well as norbornenylhydrocarbylene boronic acid embodiments (including ester derivatives thereof) and norbornenylhydrocarbylene borate embodiments represented by Formulae (II) and (III), respectively, that can be derived from a norbornenylhydrocarbylene dihydrocarbylborane represented by Formula (I):

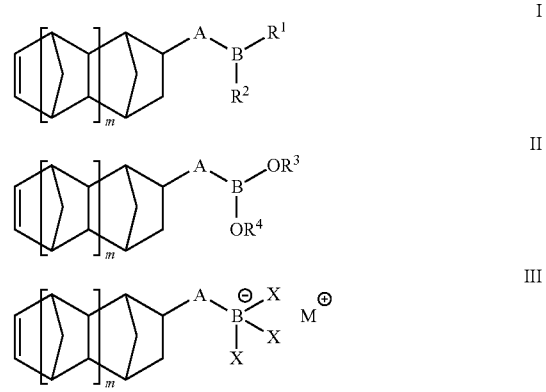

where, for Formulae (I) and (II), each of $R^1$ and $R_2$ and each of $R^3$ and $R^4$ are independently selected from a substituted or unsubstituted $C_1$ to $C_{12}$ hydrocarbyl, including but not limited to, disiamyl and thexyl groups, substituted or unsubstituted, monocyclic or bicyclic $C_5$ to $C_7$ rings, including but not limited to, 2-pinene and methylcyclopentyl. $R^3$ and $R^4$ can also be hydrogen. Additionally, $R^1$ and $R^2$ taken together with the boron atom, and $R^3$ and $R^4$ taken together with the boron and the oxygens to which they are attached, can form a monocyclic or bicyclic ring. For each of Formulae (I), (II) and (III), m is 0, 1 or 2, and A is a divalent $C_2$ to $C_{12}$ hydrocarbylene radical; Formula (I) is subject to the proviso that when $R^1$ and $R^2$ taken together with the boron atom do not form 9-borabicyclo[3.3.1]nonane when m=0. Thus from Formula (I) (9-norbornenylethyl-9-borabicyclo[3.3.1]nonane) is specifically excluded, and for Formula (III), X is a halogen, e.g., fluorine, and M is a cation, e.g., a cation of an alkali metal.

As mentioned above, the compounds of Formula (II) and (III) can be formed from a trihydrocarbylborane in accordance with Formula (I). Thus as reported by A. V. Kalinin, et al. in Angew. Chem. Int. Ed. 2003, 42, 3399-3404, treatment of a di(isopropylprenyl) containing trihydrocarbylborane with aqueous formic acid provides access to boronic acids and their derivatives, such as would be represented by Formula (II). As for compounds represented by Formula (III), G. A. Molander, et al. reported in Acc. Chem. Res., 2007, 40, 275-286, that treatment of a di(isopropylprenyl) containing trihydrocarbylborane with $KHF_2$ in acetone provided a potassium trifluoroborate, such as would be represented by Formula (III).

As previously mentioned, embodiments in accordance with the present invention also encompass making the norbornenylhydrocarbylene dihydrocarbylboranes of Formula (I). Such embodiments encompass generating a desired dihydrocarbylborane, represented as Formula A, where $R^1$ and $R^2$ are as previously defined,

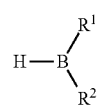

and reacting such dihydrocarbylborane with an appropriate alkenylnorbornene-type compound, represented by Formula B, where A* is a $C_2$-$C_{12}$ hydrocarbyl group containing at least one C—C double bond, and m is as previously defined.

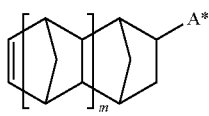

Said dihydrocarbylborane is selected such that it demonstrates enhanced regiostereochemical selectivity (as defined above) to generate a trihydrocarbylborane, such as represented by Formula (I), that is produced with at least 90 mol % selectivity when compared with all other possible trihydrocarbylboranes that can be produced by such a reaction. In some such embodiments, the trihydrocarbylborane of Formula (I) is a desired norbornenylhydrocarbylene dihydrocarbylborane generated with at least 95 mol % selectivity when compared with all other generated trihydrocarbylboranes, in other such embodiments, the desired norbornenylhydrocarbylene dihydrocarbylborane generated is at least 97 mol % of all generated trihydrocarbylboranes and in still other such embodiments, the desired norbornenylhydrocarbylene dihydrocarbylborane generated is at least 99 mol %. Generally, a desired dihydrocarbylborane is generated by reacting a borane and an unsaturated, substituted or unsubstituted cyclic hydrocarbon of at least 4 carbon atoms or an unsaturated, substituted or unsubstituted acyclic hydrocarbon of at least 5 carbon atoms. It should be noted, however, that embodiments in accordance with the present invention do not include 9-BBN (9-boracyclo[3.3.1]nonane).

For example, embodiments for making essentially pure exo-5-(2-hydroxyethyl)-2-norbornene are disclosed herein. Such method embodiments encompass first reacting borane ($BH_3$ or $B_2H_6$) with an unsaturated organic compound selected from, cyclopentene, 3,5-dimethylcyclopentene, 2,5-dimethylhexa-2,4-diene, cyclohexene, 2-methylcyclohexene, 3,6-dimethylcyclohexene, 2-methyl-2-butene, and 2-pinene (2,6,6-trimethylbicyclo[3.1.1]hept-2-ene) to form respectively one of dicyclopentylborane, di(3,5-dimethylcyclopentyl)borane, diisopropylprenyl borane, dicyclohexylborane, di(2-methylcyclohexyl)borane, di(3,6-dimethylcyclohexyl)borane, di(siamyl)borane and di(isopinocampheyl) borane. Such method embodiments further encompass second reacting a selected dihydrocarbylborane with exo-vinylnorbornene, to generate the appropriate (2-(exo-bicyclo[2.2.1]hept-5-en-2-yl)ethyl)dicyclopentylborane in at least 95% yield of all trihydrocarbylboranes, and subsequently hydrolyzing such dihydrocarbylborane to exo-5-(2-hydroxyethyl)-2-norbornene, where the exo-5-(2-hydroxyethyl)-2-norbornene is at least 95 mol % of all converted trihydrocarbylboranes. While the forming of dihydrocarbylboranes via a reaction with borane has been described, in some embodiments of the present invention, dihydrocarbylboranes are formed by other pathways as will be described in more detail herein below. For example, dihydrocarbylboranes, such as dimesitylborane and di(tri(isopropyl)phenyl)borane, where the hydrocarbyl is an aryl group forming the dihydrocarbylboranes generally involves a Grignard intermediate.

Advantageously, it has also now been found that borane ($BH_3$ or $B_2H_6$) can conveniently be generated in situ, thus avoiding direct handling of borane, which additionally provides a cost effective way to practice this invention. Any of the methods known in the literature can be used to form borane in situ, which can then be used to form a desired dihydrocarbylborane, represented as Formula A, as described above. A non-limiting example of such an in situ formation of borane includes for example reaction of a variety of borohydrides with a suitable Lewis acid or the like agents and/or a suitable reducing agent. Exemplary borohydrides that are suitable for this purpose include without any limitation alkali metal borohydrides, such as lithium borohydride, sodium borohydride, potassium borohydride, and the like. Exemplary Lewis acids that can be employed include without any limitation aluminum chloride, aluminum bromide, boron trichloride, boron trifluoride, and the like. Suitable reducing agents that can be employed include without any limitation dialkyl sulfate, such as dimethyl sulfate. Other agents that can also be used with borohydrides include halogens such as iodine or bromine, alkyl halides such as methyl iodide, mercury chloride, trimethylchlorosilane, and Bronsted acids such as phosphoric acid. In an embodiment of this invention sodium borohydride and dimethyl sulfate are used to form borane in situ. The borane thus formed can then be reacted with a desired alkene to form the compound of Formula A, which is then reacted with a suitable alkenylnorbornene-type compound of Formula B to generate a trihydrocarbylborane of Formula (I) as disclosed herein. Accordingly, by practice of this invention it is now possible to avoid use of expensive borane and in addition, the reaction sequence as described herein can be carried out in a continuous flow system, thus avoiding the use of hazardous materials in an industrial scale operation. Most advantageously, as already mentioned above, by practice of this invention highly selective terminal substituted norbornene-type compounds can be made in an industrial scale. For various literature references for the in situ formation of borane see for example, Chem. Rev., (1976), 76(6), 773; J. Org. Chem., (1969), 34, 3923; and Angew. Chem. Int. Ed., (1989), 28, 218; pertinent parts of these references are incorporated herein by reference.

Thus embodiments in accordance with the present invention encompass both the generation and use of norbornenylhydrocarbylene dihydrocarbylboranes, as represented by Formula (I) and that have the characteristics that will be discussed in detail hereinafter, for the synthesis of norbornene-type monomers that in turn are useful for the synthesis of norbornene-type polymers and other norbornene-type monomers.

As discussed above, embodiments of the present invention relate to norbornenylhydrocarbylene dihydrocarbylboranes, represented by Formula (I), norbonenylhydrocarbylene dialkenylboronic acid embodiments (including ester derivatives thereof), represented by Formula (II), and norbornenylhydrocarbylene 1-borate embodiments, represented by Formula (III), as well as methods for selectively making any norbornenylhydrocarbylene species according to Formulae (I)-(III) and the second and third generation products therefrom. That is to say that the aforementioned embodiments are inclusive of products derived directly from any species according to Formulae (I), any product in accordance with Formulae (II) or (III) (a first generation product), any product derived directly from any species according to Formula (I)-(III) not including the aforementioned first generation products (a second generation product), and any product derived directly from such second generation product (a third generation product).

Some embodiments of the present invention also encompass a norbornenylhydrocarbylene dihydrocarbylborane selected from exo-norbornenylethyldicyclohexylborane, mixtures of endo- and exo-norbornenylethyldicyclohexylborane, exo-norbornenylethyldimesitylborane, endo-norbornenylethyldimesitylborane, mixtures of endo- and exo-norbornenylethyldimesitylborane, exo-norbornenylbutyldicyclohexylborane, endo-norbornenylbutyldicyclohexylborane, mixtures of endo- and exo-norbornenylbutyldicyclohexylborane, exo-norbornenylhexyldicyclohexylborane, endo-norbornenylhexyldicyclohexylborane, mixtures of endo- and exo-norbornenylhexyldicyclohexylborane, exo-norbornenylbutyldimesitylborane, endo-norbornenylbutyldimesitylborane, mixtures of endo- and exo-norbornenylbutyldimesitylborane, exo-norbornenylhexyldimesityl borane, endo-norbornenylhexyldimesityl borane, and mixtures of endo- and exo-norbornenylhexyldimesitylborane.

Some other embodiments in accordance with the present invention encompass a norbornenylhydrocarbylene dihydrocarbylborane selected from exo-norbornenylethyldicyclohexylborane, exo-norbornenylethyldimesitylborane, exo-norbornenylbutyldicyclohexylborane, exo-norbornenylhexyldicyclohexylborane, exo-norbornenylbutyldimesitylborane, and exo-norbornenylhexyldimesityl borane.

Still other embodiments of the present invention encompass a norbornenylhydrocarbylene dihydrocarbylborane selected from endo- and exo-norbornenylethyldicyclohexylborane, endo- and exo-norbornenylethyldimesitylborane, endo- and exo-norbornenylbutyldicyclohexylborane, endo- and exo-norbornenylhexyldicyclohexylborane, endo- and exo-norbornenylbutyldimesitylborane, and endo- and exo-norbornenylhexyldimesityl borane. Embodiments of the present invention also encompass the norbornenylhydrocarbylene dihydrocarbylborane being chosen from exo-norbornenylethyldicyclohexylborane, endo-norbornenylethyldicyclohexylborane, exo-norbornenylethyldimesitylborane, endo-norbornenylethyldimesitylborane, endo- and exo-norbornenylbutyldicyclohexylborane, endo- and exo-norbornenylhexyldicycloborane, endo- and exo-norbornenylbutyldimesitylborane, and endo and exo-norbornenylhexyldimesityl borane.

Yet other embodiments in accordance with the present invention encompass a norbornenylhydrocarbylene boronate ester, represented by Formula (II), where $R^3$ and $R^4$, together with the boron and oxygen atoms, form either pinacol boronate, a substituted or unsubstituted borinyl, or a substituted or unsubstituted catechol boronate. Such embodiments are represented by Formulae (IV) through (VIII), respectively:

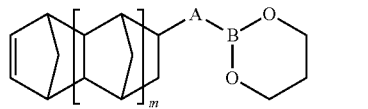

IV

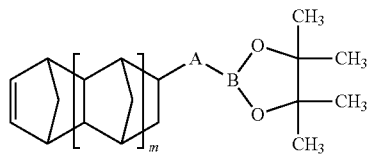

V

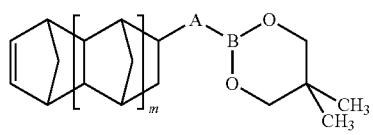

VI

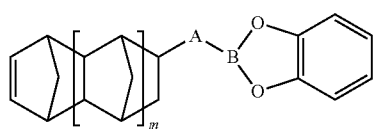

VII

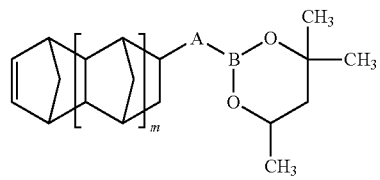

VIII

Without wishing to be bound by theory, it is believed that certain dihydrocarbylboranes may be inhibited from addition of B—H across the norbornene double bond and may thus favor the addition of B—H across a terminal double bond (i.e., one within a substituent on the norbornene ring). Such a selective addition can permit the preparation of regiostereochemical selective norbornenylhydrocarbylene dihydrocarbylboranes in very high yields.

Applicants have discovered that a correlation may exist between this selectivity of certain dihydrocarbylboranes and at least one characteristic of the dihydrocarbylborane chosen from carbon-boron-carbon (C—B—C) angle (calculated using molecular mechanics or measured by single crystal neutron or X-ray diffraction), steric interactions between reactants (determined by the proximity of atomic Van der Walls radii in transition state calculations described herein), $(R^1)(R^2)BH$ preparation and isolation method, and from $^{11}B$ NMR studies, as discussed herein, each of which may reflect steric bulk (i.e., steric requirements of the groups on the boron atom).

1. Carbon-Boron-Carbon (C—B—C) Bond Angle

Molecular geometry or molecular structure is the three-dimensional arrangement of the atoms that constitute a molecule. It determines several properties of a substance including its reactivity. The molecular geometry can be determined by various spectroscopic methods and diffraction methods. IR, microwave and Raman spectroscopy can give information about the molecule geometry from the details of the vibrational and rotational absorbance detected by these techniques. X-ray crystallography, neutron diffraction, and electron diffraction can give molecular structure for crystalline solids based on the distance between nuclei and concentration of electron density. NMR methods can be used to determine complementary information including relative distances, dihedral angles, angles, and connectivity. Molecular geometries are best determined at low temperature because at higher temperatures the molecular structure is averaged over more accessible geometries. Larger molecules often exist in multiple stable geometries (conformational isomerism) that are close in energy on the potential energy surface. Geometries can also be computed by ab initio quantum chemistry methods to high accuracy. The molecular geometry can be different as a solid, in solution, and as a gas.

The position of each atom is determined by the nature of the chemical bonds by which it is connected to its neighboring atoms. The molecular geometry can be described by the positions of these atoms in space, evoking bond lengths of two joined atoms, bond angles of three connected atoms, and torsion angles (dihedral angles) of three consecutive bonds.

Disclosed herein are the carbon-boron-carbon angles which were obtained from published literature and database information and those which we calculated using molecular modeling, e.g., Chem3D Pro Version 12.0 (basic) and DMol$^3$ (advanced).

By way of non-limiting example, the calculated (rounded to one decimal place) carbon-boron-carbon angles of various dihydrocarbylboranes are shown below in Table 1 obtained using Chem3D Pro Version 12.0.2.1076/ChemDraw Ultra 12.0 Ultra software (CambridgeSoft/PerkinElmer, Cambridge, Mass., USA) and compared to measured C—B—C angles obtained from single crystal structural analysis. Geometric optimization and energy minimization were achieved using the default MM2 force field settings and converging to a minimum (root mean square) RMS gradient of 0.010.

DMol$^3$ is first-principles (ab initio) quantum chemistry software which can perform (i) Geometry Optimization, (ii) Transition-state Searches, (iii) Single-point Energy Calculations, and (iv) Molecular Dynamics (additional information can be obtained from Accelrys, Inc. San Diego, Calif., USA). Calculations of the total energies and optimized geometries, and molecular properties were performed using density functional theory (DFT) as implemented in the DMol$^3$ software (Delley, B. J. Chem. Phys. 2000, 113, 7756). The exchange correlation energy was calculated using the local density approximation (LDA) (Kohn, W.; Sham, L. J. Phys. Rev. 1965, 140, A1133) with the parametrization of Perdew and Wang (Perdew, J. P.; Wang, Y. Phys. Rev. B 1992, 45, 13244). The generalized gradient approximation (GGA) was also used (Perdew, J. P. Phys. Rev. B 1986, 33, 8822; Becke, A. D. J. Chem. Phys., 1988, 88, 2547; and Perdew, J. P.; Wang, Y. Phys. Rev. B, 1992, 45, 13244). Double numerical basis sets including polarization functions on all atoms (DNP) were used in the calculations. The DNP basis set corresponds to a double-ζ quality basis set with a p-type polarization function added to hydrogen and d-type polarization functions (DND) added to heavier atoms. The basis set files included version 4.4 and version 3.5 (Delley, J. Phys. Chem. A, 2006, 110, 13632).

To discuss the structural properties of complexes, we compare our results obtained with DFT in Tables 1, 2, and 3 with the available experimental information. For all the systems studied the calculated geometrical properties are in good agreement with the experimental data for the crystalline structures and consistent with theoretical results obtained by calculations. In particular, our results agree very well with the results obtained by the most refined quantum chemistry method which is an indication that the chemistry is correctly described by the DFT approximation.

Alternatively, carbon-boron-carbon angle can be obtained from solid state structures of dihydrocarbylborane monomeric units [(R$^1$R$^2$BH)], dimer units [(R$^1$R$^2$BH)$_2$], and dihydrocarbylborane Lewis Base (LB) adducts [(R$^1$R$^2$BH.LB)], where R$^1$ and R$^2$ are as defined herein. The solid state structures can be obtained using the known techniques of single crystal neutron or X-ray diffraction in order to determine the arrangement of atoms within a crystal. The Cambridge Structural Database (CSD) available through The Cambridge Crystallographic Data Centre 12 Union Road, Cambridge, CB2 1EZ, UK, contains data for organic and metal-organic compounds studied by X-ray and neutron diffraction and is the repository of small molecule crystal structures and structural information about various R$^1$R$^2$BH, (R$^1$R$^2$BH)$_2$, and R$^1$R$^2$BH.LB compounds.

TABLE 1

C-B-C Bond Angles of Dialkylboranes

|  | Calculated | Measured |
|---|---|---|
| Boretane | 109.7 |  |
| Borolane | 110.7 |  |
| 9-BBN | 112.4 | 111.8[a] |
| Borinane | 118.2 |  |
| (Hexyl)$_2$BH | 120.1 |  |
| (Menthyl)$_2$BH | 120.2 |  |
| (Me$_2$CCMe)$_2$BH | 120.4 |  |
| Et$_2$BH | 120.7 |  |
| (MeCy)$_2$BH | 120.7 |  |
| Borocane | 120.9 |  |
| Borepane | 121.2 |  |
| Boronane | 121.4 |  |
| (i-Pr)$_2$BH | 121.5 |  |
| Me$_2$BH | 121.6 |  |
| Cy$_2$BH | 121.6 | 119.0[b] |
| (Cy)(tert-But)H | 122.0 |  |
| Borecane | 122.1 |  |
| (Thexyl)(Cp)BH | 123.3 |  |
| NB$_2$BH | 124.5 |  |
| (Diisocamphoryl)$_2$BH | 125.4 | 126.7[b] |
| (Me$_3$C)$_2$BH | 127.9 |  |
| (2-MeCp)$_2$BH | 130.6 |  |
| Borinane Dimer | 131.8 |  |

[a]Brauer, D. J. & Kruger, C. (1973) Acta Cryst. B29, 1684-1690 and S. Sabo-Etienne Journal of Organometallic Chemistry 680 (2003) 182-187.
[b]Richard Mynott et al. Chem. Eur. J. 2007, 13, 8762-8783.

TABLE 2

C-B-C Bond Angles of Dialkylborane Lewis Base Adducts

|  | Calculated |
|---|---|
| 9-BBN-quinoline | 103.8 |
| 9-BBN-quinoxaline | 104.0 |
| 9-BBN-2-Mepy | 104.6 |
| 9-BBN-2,6-Me2py | 104.7 |
| 9-BBN-2-Me,5-Etpy | 104.9 |
| (Me$_2$CCMe)$_2$BH-2-MePy | 112.9 |
| Cy$_2$BH-(2-Me,5-EtPy) | 113.4 |
| Cy$_2$BH-quinoxaline | 113.7 |
| Cy$_2$BH-(3-MePy) | 114.4 |
| Cy$_2$BH-Py | 114.4 |
| Cy$_2$BH-(2-MePy) | 114.5 |
| Cy$_2$BH-(4-MePy) | 114.9 |
| Cy$_2$BH-quinoline | 114.9 |
| (Diisocamphoryl)$_2$BH-2MePy | 115.2 |
| Cy$_2$BH-(2,6-Me$_2$Py) | 115.3 |
| (Diisocamphoryl)$_2$BH-2,6-Me2Py | 121.2 |

TABLE 3

C-B-C Bond Angles of Diarylboranes

|  | Calculated | Measured |
|---|---|---|
| (o-tol)$_2$BH | 120.4 |  |
| (C$_6$F$_5$)$_2$BH | 121.5 | 121.6[c] |
| (2,6-Me$_2$Ph)$_2$BH | 122.8 |  |
| (Mes)$_2$BH | 122.9 | 123.2[d,e] |
| (Trip)$_2$BH | 124.6 | 128.0[e] |
| (Ph)$_2$BH | 127.3 |  |
| (2,6-diisopropylPh)$_2$BH | 128.3 |  |

[c]Warren E. Piers et al. Organometallics 1998, 17, 5492-5503.
[d]Todd B. Marder et al. Journal of Organometallic Chemistry 680 (2003) 165-172.
[e]P. Power et al. Organometallics, 1990, 9, 146-150.

By way of example, and without limitation, the calculated carbon-boron-carbon angles of various dihydrocarbylboranes, shown in Table 4, were obtained employing the DMol$^3$ software. Where the C—B—C bond angles are shown in degrees and the B—H, B—C and B-LB bond lengths in Angstroms (Å).

TABLE 4

| Compound | Type | Calculated | | | | Single Crystal |
| --- | --- | --- | --- | --- | --- | --- |
| | | C—B—C Angle | B—H | B—C | B L B | C—B—C Angle |
| (9-BBN)BH | Monomeric | 112.02 | 1.21 | 1.56 | — | — |
| $Cy_2BH$ | Monomeric | 122.73 | 1.22 | 1.55 | — | — |
| $n\text{-}Bu_2BH$ | Monomeric | 121.57 | 1.22 | 1.55 | — | — |
| $(o\text{-}Tolyl)_2BH$ | Monomeric | 122.86 | 1.22 | 1.53 | — | — |
| $[(9\text{-}BBN)BH]_2$ | Dimeric | 111.42 | 1.33 | 1.57 | — | 111.50/111.73[f] |
| $[Cy_2BH]_2$ | Dimeric | 118.34 | 1.33 | 1.58 | — | 118.96[g] |
| $[Bu_2BH]_2$ | Dimeric | 120.58 | 1.32/1.32 | 1.58 | — | — |
| $[(o\text{-}Tolyl)_2BH]_2$ | Dimeric | 116.72 | 1.33 | 1.56 | — | — |
| (9-BBN)BH•2MePy | Lewis Base Adduct | 105.36 | 1.23 | 1.61/1.62 | 1.57 | — |
| $Cy_2BH$•2MePy | Lewis Base Adduct | 117.13 | 1.23 | 1.62/1.63 | 1.58 | — |
| $Bu_2BH$•2MePy | Lewis Base Adduct | 113.53 | 1.23 | 1.61/1.62 | 1.59 | — |
| $(o\text{-}Tolyl)_2BH$•2MePy | Lewis Base Adduct | 116.33 | 1.23 | 1.61 | 1.6 | — |

[f] S. Sabo-Etienne Journal of Organometallic Chemistry 680 (2003) 182-187.
[g] Richard Mynott et al. Chera. Eur. J. 2007, 13, 8762-8783.

Surprisingly it has now been found that monomeric dihydrocarbylborane embodiments in accordance with the present invention are characterized by having (i) a carbon-boron-carbon angle of greater than 113 degrees (measured single crystal X-ray or neutron data); and/or (ii) a carbon-boron-carbon angle of greater than 113 degrees (DMol³ calculated carbon-boron-carbon angle).

Similarly, dimeric dihydrocarbylborane embodiments in accordance with the present invention are characterized by having a DMol³ calculated C—B—C angle greater than 112 degrees. Such embodiments also encompass diarylborane or diaralkylborane dimers having a measured C—B—C angle of greater than 113 degrees as well as dialkylborane Lewis Base adducts having a measured C—B—C angle of greater than 106 degrees.

2. Isolation Method for Dihydrocarbylboranes

Embodiments of the present invention also encompass the dihydrocarbylboranes being capable of becoming solid. Embodiments of the present invention encompass the dihydrocarbylborane being dicyclohexylborane dimer, bis(dimesityl)borane, di(isopinocampheyl)borane dimer, and monomeric bis(tri-isopropylphenyl)borane. Solid forms can be desirable so that any reagents used in their preparation and the more soluble monohydrocarbyl and/or trihydrocarbylborane products can be easily washed away leaving an essentially pure dihydrocarbylborane dimer. In addition, solid forms may prevent any redistribution of the dihydrocarbylborane to monohydrocarbyl or trihydrocarbylborane which might reduce the regioselectively of the reaction to the terminal carbon. Accordingly, in at least one embodiment of the present invention, the dihydrocarbylborane is solid at room temperature.

3. $^{11}B$ NMR Chemical Shifts

The relatively fast relaxation rates and high isotopic abundance of $^{11}B$ make this nuclei well suited for quantitative analysis of boron containing compounds by NMR. The well documented chemical shifts and BH coupling constants of various $R^1R^2BH$, $(R^1R^2BH)_2$, and $R^1R^2BH.LB$ complexes as described herein can provide information regarding both coordination number of the boron as well as qualitative information regarding the nature of the $R^1$ and $R^2$ moieties. In particular, within a particular homologous series (e.g., series $R^1R^2BH$, where both $R^1$ and $R^2$ are the same aliphatic hydrocarbyl group) Lewis acidity, and by extension chemical shift in a coordinating solvent, can potentially correlate well with the steric/inductive properties of the group(s) $R^1$ and $R^2$.

The following collection of $^{11}B$ NMR chemical shifts (Table 5) is selected from a compilation reported by the Prof. T. Cole: (tcole@sciences.sdsu.edu) at San Diego State University. Comparison of chemical shifts is instructive where dialkyl and trialkylboranes are derived from the same or similar alkyl group, and where $R^1$ and $R^2$ taken together with the boron atom form a cyclic ring.

TABLE 5

$^{11}B$ NMR Chemical Shifts for $(R^1)(R^2)BH$ and $[(R^1)_3B)]$ compounds in THF and reported relative to $BF_3$•$Et_2O$ 28.0

30.0

31.6

30.5

TABLE 5-continued $^{11}$B NMR Chemical Shifts for $(R^1)(R^2)BH$ and $[(R^1)_3B)]$ compounds in THF and reported relative to $BF_3 \cdot Et_2O$

| Structure | Shift |
|---|---|
| [CH$_2$CH$_2$CH$_2$CH$_3$]$_3$B | 84.5 |
| [isobutyl]$_3$B | 84.7 |
| [cyclopentyl]$_3$B | 84.0 |
| [cyclohexyl]$_3$B | 80.8 |

In the case of coordinating solvents (e.g., THF), $^{11}$B chemical shift is inversely proportional to the strength of solvent coordination. Strong solvent coordination results in an upfield shift due to shielding of the magnetic field from the electrons of the coordinated solvent heteroatom. In general, as the bulk of substituents covalently bound to the boron atom in the hydrocarbylborane increases solvent coordination is inhibited and the $^{11}$B signal will shift downfield (increasing ppm). This is exemplified in Table 5 with about 50 ppm shift between the $(R^1)(R^2)BH$ and $(R^1)_3B$ compounds shown. A similar shift is observed between $H_2BR^1$ and $HB(R^1)_2$. The presence inductive groups (those containing aromatic, and/or heteroatom containing groups), can cause a further, albeit lesser shift in either an upfield or downfield direction. Thus depending on whether the substituent is electron withdrawing or electron donating the signal can be shifted in the up- or downfield direction, respectively, by as much as 10 ppm.

$^{11}$B NMR signals may vary based on the nature of the solvent, temperature, purity and structure (e.g., monomeric or dimeric or Lewis base adduct) of the dihydrocarbylborane compound. The $^{11}$B measurements presented in the disclosed invention correspond to dilute (1-100 mmol) THF solutions at 298 K and 1 atm unless otherwise noted. Most structure vs. activity relations are captured well by available room temperature solution NMR measurements, however in certain anomalous exceptions (e.g., structurally confined $HBR_2$ geometries) a combination of ab initio calculations and chemical intuition provide insight to identification of regioselective hydrocarbylborane reagents.

Table 5 also shows the statistically anomalous chemical shift of 9-BBN relative to other $HB(R^1)_2$ compounds from a representative series of non-geometrically constrained $HB(R^1)_2$ compounds. In accordance with one specific embodiment of this invention, the $^{11}$B NMR chemical shift for dimer 9-BBN appears at $\delta 28.0$ and a measured C—B—C bond angle of 117°, and when reacted with vinylnorbornene leads to a 70:30 selectivity for the vinyl versus the NB bond. In contrast, dicyclohexylborane dimer has a chemical shift of $\delta 30.5$ and a measured C—B—C bond angle of 119°. This modest change in substituents/bond angle affects such a significant increase in electrostatic and Van der Waals interactions that reaction with vinylnorbornene results exclusively with reaction of the vinyl double bond. Thus, in one embodiment the dihydrocarbylborane has a $^{11}$B NMR signal greater than 28 ppm (THF). There do exist exceptions to this THF chemical shift restraint and in such cases more complicated NMR experiments and/or ab initio modeling of the hydroboration transition states is used to estimate the regioselectivity of a hydrocarbylborane reagent.

4. Thermochemical Calculations

In another embodiment of this invention, there is also provided a method for predicting the selectivity of forming the compounds of Formula (I) by the reaction of a suitable borane of Formula A. Accordingly, in this embodiment of the invention ab-initio calculations were performed using the Gamess, NWchem and Gaussian 09 software packages. Reactants, products and transitions states for the reaction of a borane, for example, of Formula A, $(R^1)(R^2)BH$ with a series of alkenyl-norbornene-type compound of Formula B are optimized at the B3LYP/6-311+G level of theory. Carbon-boron-carbon (C—B—C) bond angles of $(R^1)(R^2)BH$ correspond to geometries optimized at this level. Equilibrium and transition state geometries are confirmed by the presence of exactly zero and one imaginary frequency, respectively, in the subsequent vibrational analysis. Enthalpies and free energies (298K) of optimized structures in the series are estimated from frequency calculations (B3LYP/6-311+G) using the harmonic oscillator and rigid rotor approximations. Estimates of vinyl addition selectivity ($k_{NB}/k_{vinyl}$) were made by comparison of calculated gas phase free energies ($\Delta G^{\ddagger}_{298K}$) for the ring and vinyl addition transition states using the relation:

$$K_{NB}/k_{vinyl} = e^{-\Delta\Delta G^{\ddagger}/RT}$$

Where, $K_{NB}$ is the rate constant for the addition of borane of Formula A to the internal double bond within the ring of Formula B, $k_{vinyl}$ is the rate constant for the addition of borane of Formula A to the side chain alkenyl double bond of Formula B, T is temperature in degree Kelvin (° K.), R is ideal gas constant and $\Delta\Delta G^{\ddagger}$ is the difference in free energy transition state of the borane addition to alkenyl double bond and the internal ring double bond.

It has now been found that by use of the above equation it is now possible to identify the desirable compounds of formula A which favors selective addition to the alkenyl double bond. Accordingly, in an embodiment of this invention it has now been found that compounds of formula A having the $k_{NB}/k_{vinyl}$ rate constant ratio of ≤0.1 results in greater than 90 percent selectivity for vinyl addition. In some other embodiments the ratio of ≤0.01 results in greater than 99 percent selectivity for vinyl addition, and yet in some other embodiments the ratio of ≤0.001 results in greater than 99.9 percent selectivity for vinyl addition.

Based on the information provided herein, one of ordinary skill in the art will be able to select monomeric dihydrocarbylboranes, $(R^1)(R^2)BH$; dimeric dihydrocarbylboranes, $[(R^1)(R^2)BH]_2$, and/or Lewis base adducts of dihydrocarbylboranes, $BH(R^1)(R^2) \cdot LB$ for the desired result using $^{11}$B experiments and ab initio calculations described herein.

Embodiments of the present disclosure also encompass the dihydrocarbylborane being chosen from dicyclopentylborane, di(3,5-dimethylcyclopentyl)borane, diisopropylprenylborane, dicyclohexylborane, di(2-methylcyclohexyl)borane, di(3,6-dimethylcyclohexyl)borane, di(siamyl)borane, di(isopinocampheyl)borane, dimesitylborane, and di(tri(isopropyl)phenyl)borane.

Methods for making norbornenylhydrocarbylene-dihydrocarbylboranes disclosed herein encompass generating a dihydrocarbylborane. Dihydrocarbylboranes, including general synthetic methods for making them, are known by those of ordinary skill in the art, e.g., hydroboration of 2 equivalents of olefin (unsaturated molecule) per $BH_3$ or reduction of $R_2BX$, where X=Cl, F, or Br. For example, Encyclopedia of Reagents for Organic Synthesis, John Wiley & Sons Ltd., which is also available online ("e-EROS"), contains information about dihydrocarbylboranes, non-limiting examples of which include borane-tetrahydrofuran ($BH_3.THF$) and borane dimethyl sulfide ($BH_3.SMe_2$). Thexylborane ($ThxBH_2$), dicyclohexylborane ($Cy_2BH$), disiamylborane ($Sia_2BH$), and dimesitylborane ($Mes_2BH$), diisopinocampheylborane ($Ipc_2BH$), diisocaranylborane ($Icr_2BH$), and cyclic boranes, for example, are also well known to one of ordinary skill in the art (See, e.g., A. V. Kalinin et al., Angew. Chem. Int. Ed. 42, 3399-3404 (2003)).

Embodiments of the present invention also encompass a dihydrocarbylborane being generated by reacting a borane and an unsaturated organic compound. The borane can be borane ($BH_3$), supplied in the form of diborane (($BH_3)_2$) or in the form of a complex with an ether, such as borane-tetrahydrofuran or borane-tetrahydropyran, or in the form of a complex with a sulfide, such as borane-dimethylsulfide, or an amine, such as, for example, borane-diethylaniline, or other reactive amine-borane complexes, such as, for example, tert-butyl-trimethylsilylamine-borane, N-ethyl-N-isopropylaniline borane, or N,N-diisopropyl-N-isopropyl-N-isobutylamine-borane.

In some embodiments, as previously mentioned above, in situ generated $[BH_3]_2$ may be employed to generate the monomeric dihydrocarbylboranes, $(R^1)(R^2)BH$; dimeric dihydrocarbylboranes $[(R^1)(R^2)BH]_2$; and Lewis base adducts of dihydrocarbylboranes, $BH(R^1)(R^2)$-LB. As noted above, methods to generate $[BH_3]$ are well known to those of ordinary skill in the art, in general such methods involve the use of readily available starting materials, such as sodium borohydride and $BF_3$ (see H. C. Brown and A. W. Moerikofer, Journal of the American Chemical Society, Vol 84, (1962), pp 1478-1484) and sodium borohydride and n-amyl bromide in diglyme (see, Example 1 of U.S. Pat. No. 4,153,672).

As already mentioned above, for some embodiments of this reaction, $BH_3$ or $BH_3$.LB can be formed in situ by the admixture of sodium borohydride and n-amylbromide in either a continuous or batchwise mode and this reagent reacted with an appropriate alkenyl-norbornene, such as vinylnorbornene, for a period time and temperature before being quenched (i.e., $NaOH/H_2O_2$) to yield the target hydroxyalkylnorbornene, e.g., endo-/exo-NBEtOH. For the purposes of the invention, a continuous microflow reactor system and process flow may be employed to intimately mix $BH_3$ or $BH_3$-adducts with olefins to generate $(R^1)(R^2)BH$ and $(R^1)(R^2)BH$-LB in situ, such as $Cy_2BH$ and $Cy_2BH.2Mepy$ and then react this species with the appropriate NBalkylene species, such as exo-VNB, and then provide for a reaction quench through $NaOH/H_2O_2$ to generate the requisite NB-alcohol, i.e., NBEtOH.

Furthermore, according to embodiments of the present invention, the unsaturated organic compound that is reacted with the borane is either a substituted or unsubstituted cyclic hydrocarbon comprising at least 4 carbon atoms or a substituted or unsubstituted acyclic hydrocarbon comprising at least 5 carbon atoms. Embodiments of the present invention also encompass the substituted or unsubstituted cyclic hydrocarbon comprising 4 to 20 carbon atoms, such as 5 to 15 carbon atoms, 6 to 10 carbon atoms, 7 to 9 carbon atoms, or 8 carbon atoms. Embodiments of the present invention also encompass the substituted or unsubstituted acyclic hydrocarbon comprising 5 to 21 carbon atoms. Embodiments of the present invention also encompass the unsaturated organic compound being coupled with Lewis base adducts.

Non-limiting examples of the substituted or unsubstituted acyclic hydrocarbons include cyclopentene, 2-methylcyclopentene, 3,6-dimethylcyclopentene, cyclohexene, 2-methylcyclohexene, 3,6-dimethylcyclohexene, norbornene, and pinene, including optically pure α-pinene. Non-limiting examples of the substituted or unsubstituted cyclic hydrocarbons include 2,3-dimethylbutene, 2-methyl-2-butene, and 2,5-dimethylhexa-2,4-diene.

Accordingly, non-limiting examples of the dihydrocarbylborane disclosed herein include di(cyclooctyl)borane, di(2-methylcyclopentyl)borane, dicyclopentylborane, di(3,5-dimethylcyclopentyl)borane, diisopropylprenylborane, dicyclohexylborane, di(2-methylcyclohexyl)borane, di(3,6-dimethylcyclohexyl)borane, dinorbornylborane, di(siamyl)borane, di(isopinocampheyl)borane, 3,6-dimethylborepane, di(o-tolyl borane, dimesitylborane, (cyclohexyl)(tert-butyl) borane, (cyclohexyl)(methyl)borane, diphenylborane, and dis(2,4,6,-triisiopropylphenyl)borane.

In at least one embodiment, the dihydrocarbylborane is complexed with a Lewis base to form dihydrocarbylborane amine complexes, such as those described in U.S. Patent Application Publication No. 2009/0256111 and PCT Publication No. WO 2009/133045. Non-limiting examples of the amine Lewis base include, but are not limited to, 2-picoline, quinoline, quinoxaline, 2,3-lutidine, 2,4-lutidine, 2,5-lutidine, 5-ethyl-2methylpyridine, 4-ethyl-2-methylpyridine, 3-ethyl-2-methylpyridine, 2,5-diethylpyridine, 5-propyl-2-methylpyridine, 4-propyl-2-methylpyridine, 5-isopropyl-2-methylpyridine, 5-t-butyl-2-methylpyridine, 5-n-hexyl-2-methylpyridine, 4-isobutyl-2-methylpyridine, and 2,4-dipropylpyridine.

As one of ordinary skill in the art would understand, synthesis of the dihydrocarbylborane can, depending on the conditions, result in an equilibrium involving the desired dihydrocarbylborane ($R_2BH$), a monohydrocarbylborane ($RBH_2$), and a trihydrocarbylborane ($R_3B$) as shown in Schemes 1a and 1b.

Scheme 1a

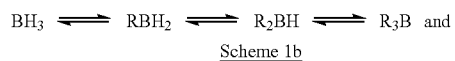

Scheme 1b

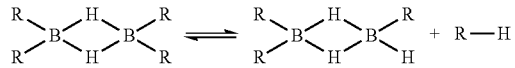

See "Hydroboration" chapter in Kirk-Othmer Encyclopedia of Chemical Technology, Vol. 13 pages 631-684 (Zaidlewicz, M. 2000. Hydroboration. Kirk-Othmer Encyclopedia of Chemical Technology). Accordingly, to generate dihydrocarbylboranes as described herein, one of ordinary skill in the art may take care to select reaction conditions that would avoid disproportionation/redistribution of the dihydrocarbylborane and/or may isolate the dihydrocarbylborane prior to reacting it. Such care is well known in the art. See, e.g., the Kirk-Othmer Encyclopedia, supra, at pp. 636-637; see also S, K. Gupta, Journal of Organometallic Chemistry 156:95-99 (1978); H. C. Brown et al., J. Am. Chem. Soc. 82:4703-4707 (1960).

Of particular relevance to the embodiments of this invention is the report by H. C. Brown and S. K. Gupta in J. Organometallic Chem., 32, (1971) C1-C4 which provides information for the general synthesis of dialkylboranes and their pyridine adducts in high yields and purity from the redistribution of organoboranes and arylborates with subsequent reduction of the dialkylborinate with lithium aluminum hydride to yield the desired dialkylboranes directly. The representative alkyl groups are 1-butyl, 2-butyl, isobutyl, cyclopentyl, cyclohexyl, and exo-norbornyl.

According to embodiments of the present invention, the dihydrocarbylborane, once generated, is then reacted with an alkenylnorbornene to generate at least one trihydrocarbylborane where such is a norbornenylhydrocarbylene dihydrocarbylborane that is at least 90 mol % of all trihydrocarbylboranes.

Embodiments of the present invention also encompass the reactant ratio (molar equivalents) of the dihydrocarbylborane to the alkenylnorbornene ranging from 1:1 to 1:200.

Although as described herein hydroboration in accordance with this invention occurs primarily at the terminal carbon of the double bond, however, one of ordinary skill in the art would understand that there could be some addition at the β (beta)-carbon. Accordingly, one of ordinary skill in the art would anticipate a small percentage of addition at the beta-carbon for NB-A-BR$^1$R$^2$ and would understand that it would not affect the selectivity of the diboranes described herein for the unsaturated bond in the substituent on the norbornene ring over the internal norbornene double bond.

According to the present invention, the alkenylnorbornene follows the general formula: NB-A* wherein A* is a $C_2$-$C_{12}$ hydrocarbylene group containing at least one C—C double bond.

Embodiments of the present invention also encompass the alkenylnorbornene being exo-vinylnorbornene, endo-vinylnorbornene, a mixture of endo-vinylnorbornene and exo-vinylnorbornene, exo-propenylnorbornene, endo-propenylnorbornene, a mixture of exo-propenylnorbornene and endo-propenylnorbornene, exo-butenylnorbornene, endo-butenylnorbornene, a mixture of exo-butenylnorbornene and endo-butenylnorbornene, exo-pentenylnorbornene, endo-pentenylnorbornene, a mixture of exo-pentenylnorbornene and endo-pentenylnorbornene, exo-hexenylnorbornene, endo-hexenylnorbornene, a mixture of exo-hexenylnorbornene and endo-hexenylnorbornene, exo-heptenylnorbornene, endo-heptenylnorbornene, a mixture of exo-heptenylnorbornene and endo-heptenylnorbornene, exo-octenylnorbornene, endo-octenylnorbornene, a mixture of exo-octenylnorbornene and endo-octenylnorbornene, exo-nonenylnorbornene, endo-nonenylnorbornene, a mixture of exo-nonenylnorbornene and endo-nonenylnorbornene, exo-decenylnorbornene, endo-decenylnorbornene, a mixture of exo-decenylnorbornene and endo-decenylnorbornene, exo-dodecenylnorbornene, endo-dodecenylnorbornene, or a mixture of exo-dodecenylnorbornene and endo-dodecenylnorbornene.

As mentioned above, embodiments in accordance with the present invention also encompass methods for further converting the norbornenylhydrocarbylene-dihydrocarbylborane other products, according to the general formula:

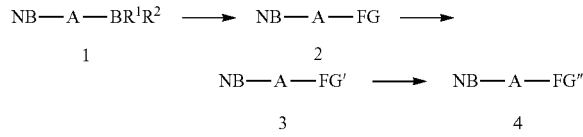

wherein FG is a functional group other than BR$^1$R$^2$. And where compounds of formula 1 are same as compounds of Formula (I) as described herein, which is also called as first generation products, and compounds of formulae 2, 3 and 4 are respectively are the second, third and fourth generation products as described herein. Various methods known in the art can be used to form these $2^{nd}$, $3^{rd}$ and $4^{th}$ generation products. For example, derivatization reactions of organoboranes are known, such as, for example, those discussed in U.S. Pat. Nos. 4,713,380 and 6,855,848, Acc. Chem. Res. 2007, 40, pp. 275-286 (G. A. Molander and N. Ellis), Tetrahedron Vol. 43. No. 18. pp. 401-4078, 1987 (H. C. Brown et al.), Chem. Rev. 2011, 111, pp. 2177-2250 (J. Magano and J. R. Dunetz). Chem. Rev. 2008, 108, pp. 288-325, (S. Darses and J-P. Genet), Angew. Chem. Int. Ed. 2003, 42, pp. 3399-3404 (A. V. Kalinin, S. Scherer, and V. Snieckus), and J. Am. Chem. Soc. 1989, 111, pp. 314-321 (N. Miyaura, T. Ishiyama, H. Sasaki, M. Ishikawa, M. Satoh, and A. Suzuki). More specifically, as already described above, the compounds of Formula (I) can be converted to corresponding alcohols, or alkyl derivatives or haloalkyl derivatives as shown by Equation 1.

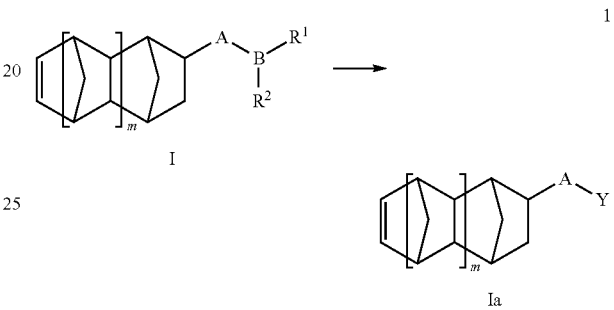

Where Y represents hydrogen, hydroxy, halogen, including iodine, bromine, chlorine, fluorine, and the like. Similarly, compounds of Formula (II) can be converted to other useful building blocks by any of the methods known in the art such as for example suitable coupling reaction to form alkyl, alkenyl, alkynyl or aryl substituted compounds in accordance with Equation 2.

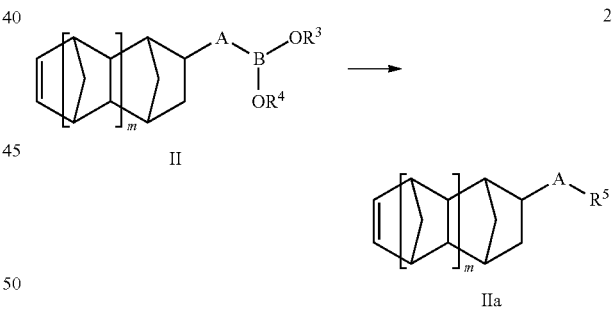

Where is R$^5$ is $C_1$ to $C_{12}$ hydrocarbyl, substituted or unsubstituted, monocyclic or bicyclic $C_5$ to $C_7$ rings, $C_2$ to $C_{12}$ alkenyl, substituted or unsubstituted, monocyclic or bicyclic $C_5$ to $C_7$ rings containing at least one double bond, which is directly connected to A, $C_2$ to $C_{12}$ alkynyl, substituted or unsubstituted, monocyclic or bicyclic $C_5$ to $C_7$ rings containing at least one triple bond, which is directly connected to A and $C_6$ to $C_{10}$ aryl.

Embodiments of the present invention also encompass the norbornenylhydrocarbylene-dihydrocarbylborane being exo-norbornenylethyldicyclohexylborane and the second generation product being exo-5-(2-hydroxyethyl)-2-norbornene. Embodiments of the present invention also encompass the norbornenylhydrocarbylene-dihydrocarbylborane being exo-norbornenylethyldicyclohexylborane and the second generation product being exo-norbornenylethylphenyl. Embodiments of the present invention also encompass the norbornenylhydrocarbylene-dihydrocarbylborane being endo-/exo-norbornenylbutyldicyclobutylborane and the second generation product being endo-/exo-5-(2-hydroxybutyl)-2-norbornene. Embodiments of the present invention also encompass the norbornenylhydrocarbylene-dihydrocarbylborane being endo-/exo-norbornenylhexyldicyclohexylborane and the second generation product being endo-/exo-5-(2-hydroxyhexyl)-2-norbornene.

The present invention also relates to a method comprising further converting the second generation product to a third generation product.

Embodiments of the present invention also encompass the second generation product being exo-NBCH$_2$CH$_2$OH and the third generation product being chosen from exo-NBCH$_2$CH$_3$, exo-/endo-NBCH$_2$CH$_3$) exo-NBCH$_2$CH$_2$Br exo-NBCH$_2$CH$_2$Cl, exo-NBCH$_2$CH$_2$I, exo-NBCH$_2$CH$_2$F, exo-NBCH$_2$CH$_2$OCH$_2$C(CF$_3$)$_2$OH and endo-/exo-NBCH$_2$CH$_2$OCH$_2$C(CF$_3$)$_2$OH. Embodiments of the present invention also encompass the second generation product being exo-NB(CH$_2$)$_4$OH and the third generation product being chosen from exo- and endo-NB(CH$_2$)$_3$CH$_3$. Embodiments of the present invention also encompass the second generation product being exo-NB(CH$_2$)$_6$OH and the third generation product being chosen from exo- and endo-NB(CH$_2$)$_5$CH$_3$. Embodiments of the present invention also encompass the second generation product being exo-NB(CH$_2$)$_4$OH and the third generation product being chosen from endo- and exo-NB(CH$_2$)$_4$OCH$_2$C(CF$_3$)$_2$OH. Embodiments of the present invention also encompass the second generation product being exo-NB(CH$_2$)$_6$OH and the third generation product being chosen from endo- and exo-NB(CH$_2$)$_6$OCH$_2$C(CF$_3$)$_2$OH.

Exemplary compounds of Formula (I) without any limitation are summarized below:

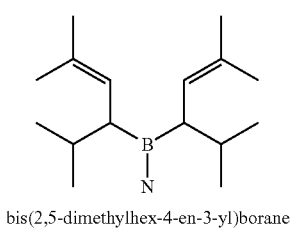

bis(2,5-dimethylhex-4-en-3-yl)borane
(diippBH)

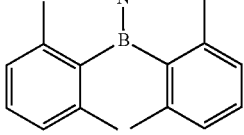

bis(2,6-dimethylphenyl)borane
(26Me$_2$Ar)$_2$BH)

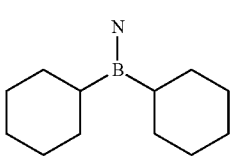

Dicyclohexylborane
(Cy$_2$BH)

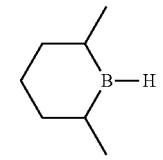

2,6-dimethylborinane
(Me$_2$Borinane)

-continued

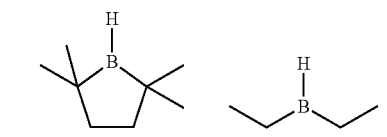

2,2,5,5-tetramethylborolane    diethylborane
(2255Me$_4$Borolane)              (Et$_2$BH)

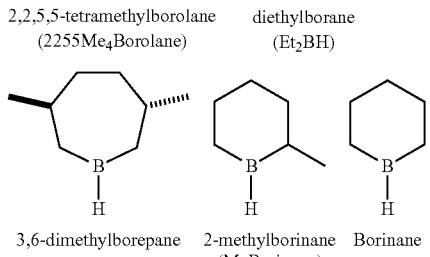

3,6-dimethylborepane    2-methylborinane    Borinane
(Me$_2$Borepane)         (MeBorinane)

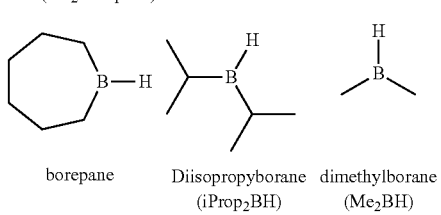

borepane    Diisopropyborane    dimethylborane
             (iProp$_2$BH)         (Me$_2$BH)

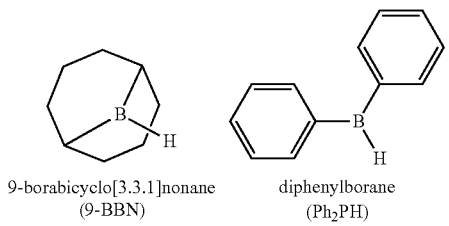

9-borabicyclo[3.3.1]nonane    diphenylborane
(9-BBN)                         (Ph$_2$PH)

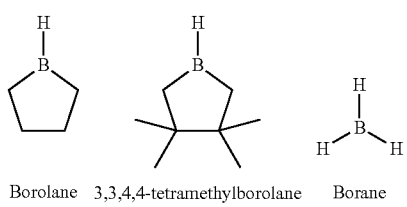

Borolane    3,3,4,4-tetramethylborolane    Borane
              (3344Me$_4$Borolane)           (BH$_3$)

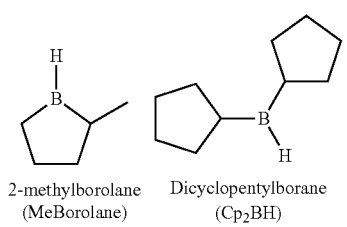

2-methylborolane    Dicyclopentylborane
(MeBorolane)         (Cp$_2$BH)

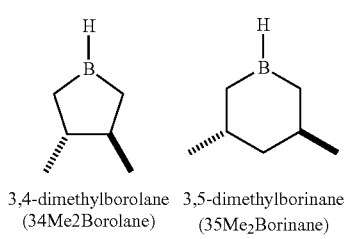

3,4-dimethylborolane  3,5-dimethylborinane
(34Me2Borolane)       (35Me$_2$Borinane)

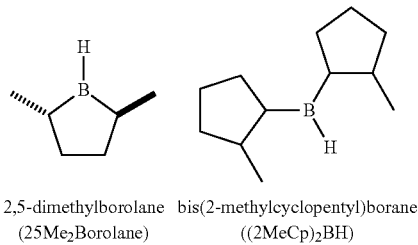

2,5-dimethylborolane (25Me₂Borolane)    bis(2-methylcyclopentyl)borane ((2MeCp)₂BH)

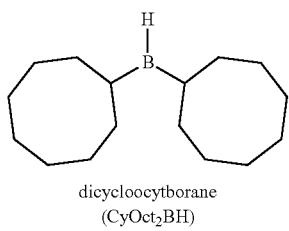

dicycloocytborane (CyOct₂BH)

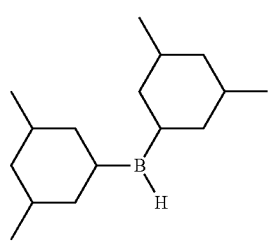

bis(3,5-dimethylcyclohexyl)borane ((35Me₂Cy)₂BH)

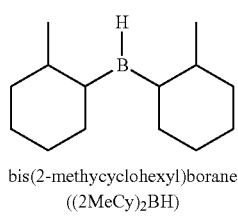

bis(2-methycyclohexyl)borane ((2MeCy)₂BH)

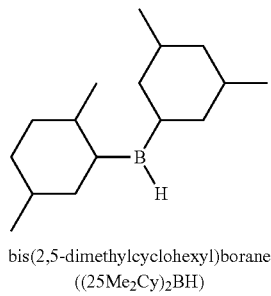

bis(2,5-dimethylcyclohexyl)borane ((25Me₂Cy)₂BH)

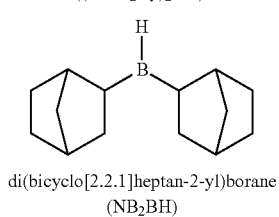

di(bicyclo[2.2.1]heptan-2-yl)borane (NB₂BH)

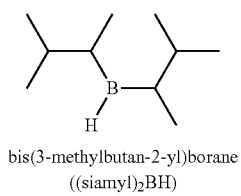

bis(3-methylbutan-2-yl)borane ((siamyl)₂BH)

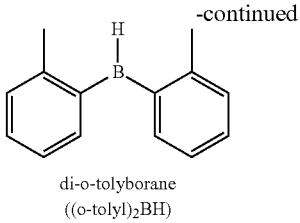

di-o-tolyborane ((o-tolyl)₂BH)

The following examples are intended to illustrate the disclosure without limiting the scope thereof.

EXAMPLES

All manipulations were carried out under and inert atmosphere (N₂ or argon) with the use of standard Schlenk tube/airless transfer techniques. In general, solvents were dried over molecular sieves or distill from a dry agent and purge with nitrogen prior to use.

The following examples are intended to illustrate the disclosure without limiting the scope thereof.

Synthesis of Organoboranes

Example B1

Synthesis of Di(isopropylprenyl)borane

The di(isopropylprenyl)borane was prepared following the literature procedure outlined in Angew. Chem. Int. Ed. 2003, 42, pp. 3399-3404. Under a nitrogen atmosphere, to a THF (3.0 mL) solution of 2,5-dimethyl-2,4-hexadiene (3 g, 17.4 mmol) at 0° C., was added a THF solution of THF.BH₃ (12.5 mL 1.0 M) slowly to maintain the temperature of mixture below 5° C. The reaction was allowed to proceed at 0° C. for 3 hours. Generally the di(isopropylprenyl)borane is not isolated but used in solution as a hydroboration reagent.

Example B2

Synthesis of Bis(3,6-dimethyl)borepane

Under a nitrogen atmosphere, 2,5-dimethyl-1,5-hexadiene (7.54 g, 68.4 mmol) was added to a THF solution of THF.BH₃ (64.5 mL 1 M) at 0° C. The reaction was allowed to proceed for an hour at 0° C., and then the reaction solution was refluxed for an hour. Generally the bis(3,6-dimethyl)borepane is not isolated but used in solution as a hydroboration reagent.

Example B3

Synthesis of Dicyclohexylborane

Under a nitrogen atmosphere, a THF solution of THF.BH₃ (21.5 mL 1 M) was added slowly to a diethyl ether (40 mL) stirred solution of cyclohexene (3.64 g, 44.3 mmol) at 0° C. The reaction was allowed to proceed for 4.5 hours at 0° C. A white precipitate was allowed to settle without stirring. The supernatant solution was removed by cannula transfer and the white solid was washed with diethyl ether. After vacuum drying, 2.48 g dicyclohexylborane was obtained (65% yield).

Example B4

Synthesis of Dicyclohexylborane-Picoline Complex

Under a nitrogen atmosphere, to a THF solution of dicyclohexylborane (8 mL, 1 M) at 0° C., was added picoline (745 mg, 8 mmol). The reaction mixture was allowed to warm room temperature. Generally the dicyclohexylborane-picoline complex is not isolated but used in solution as a hydroboration reagent.

Example B5

(Exo-Norbornenylethyl)dicyclohexylborane

A three-neck 2-L flask fitted with mechanical stirrer, graduated addition funnel, and Claisen head holding a thermowell and nitrogen inlet adapter, was dried to 120° C. under a nitrogen flush. After cooling to room temperature, borane-dimethylsulfide (EDMS) (69.4 g, 93%, 0.85 mol) was transferred by cannula into the addition funnel and then dropped into the reaction flask. The BDMS was stirred as 400 ml anhydrous diethyl ether was added via the addition funnel. The solution was cooled to −9° C. before adding cyclohexene (143.8 g, 1.75 mol) drop wise. Precipitation occurred after ∼½ of the cyclohexene had been added. Addition time was 37 minutes with the temperature ranging from −10 to +4° C. The mixture was allowed to stir for about 3 hrs between −1 to 15° C. The mixture was cooled to −10° C. and exo-vinylnorbornene (102.1 g, 0.85 mol) was added quickly over a 7 minute period. The cooling bath was removed and the mixture was allowed to warm to room temperature. Near room temperature, the mixture cleared and warmed quickly to 34° C. The solution was allowed to stir overnight. NMR analysis as the alcohols gave a 33:67 ratio of NBEtOH:cyclohexanol. GC analysis indicated a 35:57 ratio of NBEtOH:cyclohexanol. The mixture was split into portions of 356 ml and 328 ml and each portion rotary evaporated to give 129 g and 119 g of (norbornenylethyl)dicyclohexylborane concentrate. Total recovered was 250 g for 98.5% yield. The 130 g portion was dissolved in 800 ml anhydrous diglyme to give a 14.9 wt. % solution. The 120 g portion was dissolved in 800 ml anhydrous THF to give a 14.7 wt. % solution.

Synthesis of Alkylenenorbornenes

Example N1

Preparation of Exo-VNB

High purity exo-vinylnorbornene (>98.5% purity) was obtained through the thermolysis of endo-exo-vinylnorbornene (endo/exo-VNB, Ineos BV, Belgium) under back-pressure control using ramped temperature and pressure within a separation column by following the procedure of Example 19 in US Patent Application Publication US 2009/0054714 (Feb. 26, 2009).

Example N2

Preparation of Endo-VNB

A modified procedure of the experimental described by T. Wipke and G. L. Goeke in J. Am. Chem. Soc. (1974), 96(13), 4244 was employed. A 1 L, 4 neck round bottom flask (RBF) was equipped with a mechanical stirrer, thermowell, septum, and condenser with nitrogen inlet. The RBF was charged with palladium chloride ($PdCl_2$) (45 g, 0.25 mol) in 450 mL anhydrous benzene. The mixture was stirred at room temperature for 18 h, filtered, washed with pentane and dried under vacuum to give 44.8 g (0.25 mol) of $PdCl_2$. The $PdCl_2$ was transferred to a 250 mL RBF under inert atmosphere and 91.1 g (0.76 mol, 3 equiv) of exo-/endo-vinylnorbornene was added and the mixture stirred at room temperature for 18 h to give an off-white thick paste. Then, 100 mL of pentane was added and the mixture stirred at room temperature for another 24 h. An off-white fluffy precipitate was filtered and washed with pentane, dried under vacuum to give 66 g (88% yield) di-µ-chloro-bis(2-exo-chloro-5-endo-vinyl-3-norbornyl)dipalladium complex with >99% purity by NMR. The brown unreacted $PdCl_2$ (6.4 g) was separated and added to another charge of exo-/endo-VNB (4 equiv.) and stirred at room temperature for 24 h. The off-white precipitate was triturated with pentane and filtered and washed with pentane. The off-white complex was dried under vacuum to give 7.6 g (10% yield) of complex with >99% purity by NMR. $^1$H NMR and $^{13}$C NMR were consistent with the structure. The combined yield for this reaction was 98%.

A 12 L RBF was equipped with a thermowell, stopper, nitrogen inlet and mechanical stirrer. The RBF was charged with di-µ-chloro-bis(2-exo-chloro-5-endo-vinyl-3-norbornyl)dipalladium (101.9 g, 0.34 mol) dissolved in 2.55 L of $CH_2Cl_2$ to give a clear pale yellow solution. The mixture was stirred and 2.55 L of 1.5 M aqueous NaCN solution was added slowly at room temperature. A slight exotherm was observed and stirring was continued for 1 h. An aliquot of the mixture was checked by NMR directly and it indicated that the reaction was completed. The clear reaction mixture was separated and the aqueous layer was extracted with $CH_2Cl_2$. The organic layers were combined, washed with brine and dried over $Na_2O_4$ and filtered through a pad of $MgSO_4$. The filtrate was distilled to remove $CH_2Cl_2$ under atmospheric pressure at 39 to 42° C. and gave 56.4 g of crude material as a light yellow oil with 32.6% residual $CH_2Cl_2$ by NMR. The crude material was transferred to a 100 ml single neck RBF, and connected to short path distillation head and distilled at 143-163° C. under atmospheric pressure to give 32 g (78% yield) of product as a clear volatile liquid with 99.8% purity by GC. $^1$H NMR, $^{13}$C NMR and MS were consistent with the desired structure of endo-vinylnorbornene.

Example N3

Endo-/exo-Butenylnorbornene

To an 8 L stainless steel autoclave reactor was charged 2.1 kg (25.6 mol) 1,5-hexadiene (>99% purity, Boulder Scientific Company). Stirring was started, and the reactor evacuated of air and padded with 5 psig nitrogen. Pleating to 200° C. commenced, and upon achieving 200° C., the reactor was held for 6.5 hours at this temperature. During this time, a mixture of 0.05 kg (0.7 mol) 1,5-hexadiene and 0.43 kg (3.3 mol) dicyclopentadiene (>99% purity, Cymetech, LLC) were added to the reactor at a constant rate of 1.24 g/min. At the end of the addition, the reactor was held 30 minutes at 200° C. and then cooled to ambient temperature and discharged. The major identified components of the charge, as measured by GC area, were: 67% 1,5-hexadiene, 0.5% dicyclopentadiene, 26% butenylnorbornene, and 0.1% cyclopentadiene trimers. A total of five reactions were completed and distilled to produce 2.4 kg butenylnorbornene with assay greater than 99% (GC area).

Example N4

Endo-/exo-Hexenylnorbornene

A charge of 1,7-octadiene (OCT, 2.35 kg, 21.32 mol) was added to a 2 gallon Parr reactor. Melted dicyclopentadiene (DCPD, 860 grams, 6.52 mol) was mixed with 140 grams of OCT into a 2 L bottle. The bottle was then placed on a balance so that the delivery weight could be monitored. The meter feed line was flushed with the DCPD/OCT mixture and then affixed and sealed into the entry port of the Parr reactor. The sealed reactor was flushed three times with nitrogen and then finally sealed with 5 psig nitrogen pressure. The mixture was stirred at 300 rpm while heating the reaction mixture to 200° C. When the temperature had stabilized at 200° C., the DCPD/OCT feed was initiated at 2.76 ml/min. The metered feed was completed in 6.5 hours with an additional 0.5 hour hold. Maximum pressure obtained was 81 psig. The mixture was cooled to 25° C. and drained from the reactor to collect 3350 grams crude product. GC analysis showed approximately 0.2% cyclopentadiene (CPD), 45% OCT, 1.2% DCPD, 37% hexenyl norbornene (NBHexe), 0.8% CPD trimer, 5.6% tetracyclododecenehexenyl (TDHexe), 6.5% Bis-Butenyl Norbornene (NBBuNB), and 2% Heavies. The above charge was repeated six times. Total crude material (19.7 kg) of hexenyl norbornene was combined into a 22 L three neck, round bottom flask and purified through 96" inch glass column sections with stainless steel Pro-Pak packing. The vacuum distillation conditions were 50-102° C. and 4-16 Torr. The distillation cuts (72% yield) contained approximately 0.03% DCPD, 99.63% NBHexe, and 0.34% Other as clear, colorless liquids.

Preparation of Functionalized Norbornene Monomers

Example F1

Exo-NBEtOH

A 3-L 4-neck flask fitted with mechanical stirrer, nitrogen inlet, thermowell, and septa-stoppered addition funnel was dried by heating to ~140° C. under a nitrogen purge. The flask was cooled to <−10° C. $BH_3.SMe_2$ (100 ml, 1.05 mol) was transferred to the addition funnel and then dropped into the chilled flask. The $BH_3.SMe_2$ was stirred as it was cooled further to −17° C. Cyclohexene (177.5 g, 2.17 mol) in 420 ml anhydrous ethyl ether was added rapidly drop wise. After the first 125 ml is added, the temperature rises to 4° C. and solid begins precipitating. Addition of cyclohexene solution was stopped when the temperature reached +1° C. and then climbed to +9° C. The reaction was rechilled to −5° C. before resuming addition of cyclohexene solution. Addition was completed in 1 hr 25 min with the temperature ranging from −17 to +9° C. The mixture was then stirred 3.5 hrs at temperatures between −6° C. to +1° C. The reaction was then cooled to −17° C. Filtered exo-5-vinylnorbornene (110.3 g, 0.918 mol) was dissolved in 250 ml anhydrous ethyl ether and then added drop wise to the slurry of dicyclohexylborane. Addition was completed in 20 minutes at temperatures between −17 to −11° C. The cooling bath was removed. The mixture was warmed to room temperature and then stirred overnight. When the reaction reached a temperature of 26° C. (a small exotherm occurred after 32 minutes of warming), the reaction mixture cleared. GC analysis after 2 hours at room temperature indicated the expected 66:32 ratio of cyclohexanol:NBEtOH, but GC analysis was inconsistent as more dilute samples showed this ratio to be 79:19. After stirring overnight, NMR analysis showed the ratio be indeed 61:39 cyclohexanol:NBEtOH.

The reaction was cooled with an acetonitrile/dry ice bath. When the temperature of the reaction mixture reached −10° C., 8 wt. % aqueous NaOH (525 ml, 1.05 mol) was added rapidly drop wise. The addition time was 16 minutes with the temperature rising to −8° C. The reaction was allowed to cool to −9° C. before adding 35% hydrogen peroxide ($H_2O_2$) (391 ml, 4.43 mol) drop wise. The addition was stopped periodically while allowing the ensuing exotherm to subside. No further exotherms occurred after 240 mol of the peroxide had been added. Addition was completed in 1 hour 42 min with the temperature ranging from −13 to −2° C. The resulting solids caked up and caused the stirrer to seize. The cooling bath was removed and upon warming, stirring was able to resume. The mixture warmed to 36° C., causing some boiling of the ether solvent. When cooled back to 28° C., 85 ml of 3.5 N HCl was added and then 57 ml of conc. HCl to bring the pH to 7. The layers were separated. The upper ether phase was dried over anhydrous sodium sulfate, filtered, and rotary evaporated to give 320 g. NMR analysis shows this contains a 32:68 mixture of NBEtOH:cyclohexanol, giving a NBEtOH content of ~40 wt. %.

The crude product was distilled in the Kugelrohr oven at 60-80° C. (1-2 torr) to remove 184 g of mainly cyclohexanol. The residue was vacuum distilled through a 12-inch glass bead-packed column with a few crystals of di-t-butylhydroquinone added to inhibit resin formation. NBEtOH was isolated, 63 g, 99% purity for 50% yield.

Example F2

5-(2-Hydroxyethyl)norbornene (NBEtOH) from trimethylamine oxide 410.04 g of 14.9 wt. % dicyclohexyl(ethylnorbornenyl)borane (0.23 mol) in anhydrous diglyme were placed in a single-necked flask fitted with a Claisen head holding a mechanical stirrer and nitrogen-inlet adapter. Trimethylamine oxide (68.3 g, 0.614 mol) was added. An immediate exotherm resulted with the temperature climbing to ~73° C. and vigorous bubbling. When the initial reaction had subsided, the mixture was heated to reflux (~172° C.) for two hours. However, off-gassing of trimethylamine had ceased only after 16 minutes of reflux. The reaction was cooled to room temperature, 100 ml brine was added, and the mixture transferred to a separatory funnel. This left behind a large amount of solid that was insoluble in ether and water, but could be broken up with 3.5N HCl. The phases were separated and the organic portion was washed with 2×150 ml brine. GC analysis of the organic phase showed 25% cyclohexanol, 66% diglyme, and 8% NBEtOH. The organic phase was vacuum distilled through a 14-inch Vigreux column to collect a total of 11.19 g NBEtOH (94% purity).

The pot residue was dissolved in dichloromethane, washed with 2×50 ml 10% sulfuric acid, 3×100 ml brine, and dried over sodium sulfate. The solution was decanted and rotary evaporated to give 12.8 g. This was vacuum distilled at 106° C. (6 Torr) to give an additional 8.6 g NBEtOH (95% purity). The total NBEtOH collected was 19.8 g for 70% yield.

Example F3

Endo-exo-norbornenebutanol

A 4-neck 1-L flask fitted with mechanical stirrer, nitrogen inlet, thermowell, and addition funnel was dried with a hot air gun. Boranedimethylsulfide (96.4%, 34 ml, 27.7 g, 0.351 mol) was transferred by nitrogen pressure into the addition funnel and then dropped into the reaction flask. Anhydrous ether (160 ml) was added via the addition funnel to the stirred borane-dimethylsulfide. The solution was cooled to −8° C. Cyclohexene (59.1 g, 0.72 mol) was added rapidly drop wise. Addition was completed within 34 minutes with the temperature ranging from −8° C. to +6.0° C. Precipitation of dicyclohexylborane occurred after the initial 7 min. of addition time.

The mixture was allowed to stir two hours between 3° C. and 23° C. The mixture was cooled to −12° C. Endo,exo-but-1-enylnorbornene (51.6 g, 0.348 mol) was added rapidly within 2 minutes. The reaction temperature rose to −9° C. The coolant bath was removed and the reaction mixture warmed to room temperature. After 12 minutes, the temperature reached to 16° C. The reaction suddenly became exothermic as the temperature rose quickly within three minutes to 33° C. maximum and the solution cleared. After 17 minutes, the temperature had dropped to 25° C. The reaction mixture was stirred at ambient temperature overnight. GC analysis showed 40.8% cyclohexanol (CyOH), 5.6% unreacted butenylnorbornenes, and 49.4% endo- and exo-norbornenebutanol. The reaction mixture was cooled to −3° C. 170.4 g 8% NaOH was added quickly within 2 minutes. The temperature rose to +7° C. The mixture was allowed to cool to +2° C. 137 ml reagent alcohol was added, causing the temperature to rise to 11° C. The resulting hazy solution was cooled to −2° C. before adding 50 ml 35% $H_2O_2$. This addition was completed in 53 minutes, causing the temperature to rise to 26° C. A second 79 ml portion of 35% $H_2O_2$ was added within 17 minutes, causing the temperature to rise to 31° C. After cooling to 17° C., the cooling bath was removed. The reaction mixture gradually warmed to 26° C. within 2 hrs and then self-cooled to 25° C. Solids had precipitated. 25 ml concentrated HCl was added to bring the pH to ~2. The mixture was stirred and then allowed to settle. The liquid portion was decanted away from the solids and the phases were separated. The organic phase was washed with 100 ml brine, 60 ml saturated sodium bicarbonate mixed with 40 ml brine, and 3×100 ml brine to pH 7. The organic phase was then rotary-evaporated from room temperature to 50° C. at 12 Torr to give 111 g liquid with solids. GC analysis showed 47.2% CyOH, 4.3% unreacted endo- and exo-butenylnorbornene, and 47.1% endo- and exonorbornenebutanol. 100 mL deionized water was added and the mixture rotary evaporated at 55° C. and 10 Torr vacuum until all water had been removed. This left the pot with 35.3% CyOH, 0.6% endo- and exo-butenylnorbornene, and 61.8% endo- and exo-norbornenebutanol. Azeotropic removal of CyOH and unreacted butenylnorbornene was repeated successively with four (4) additional 100 ml treatments with distilled water to give a pot totaling 50.63 g which contained 1.5% CyOH, no butenylnorbornene, and 95.3% endo- and exo-norbornenebutanol. The mixture was vacuum distilled slowly through a 6.5-inch Hempel column packed with 4-inches of <7 mm i.d. glass helices. The total yield of CyOH-free endo-,exo-NBBuOH was 37.63 g (65% yield). GC analysis showed 85:15 and 81:19 endo:exo ratio for two fractions and NMR analysis indicated an endo:exo ratio of 76:24.

Example F4

Endo-exo-norbornenehexanol

A 4-neck 1-L flask fitted with mechanical stirrer, nitrogen inlet, thermowell, and addition funnel was dried with a hot air gun. Boranedimethylsulfide (96.4%, 29 ml, 23.1 g, 0.293 mol) was transferred by nitrogen pressure into the addition funnel and then dropped into the reaction flask. Anhydrous ether (130 ml) was added via the addition funnel to the stirred borane-dimethylsulfide. The solution was cooled to −12° C. Cyclohexene (48.1 g, 0.586 mol) was added rapidly drop wise. Addition was completed within 13 minutes with the temperature ranging from −12° C. to +4° C. Precipitation of dicyclohexylborane occurred after the initial 8 min. of addition time. The mixture was allowed to stir two hours between 4° C. and 24° C. The mixture was cooled to −5° C. Endo, exo-hex-1-enylnorbornene (50 g, 0.284 mol) was added rapidly within 5 minutes. The reaction temperature cooled to −7° C. The coolant bath was removed and the reaction mixture warmed to room temperature. After 18 minutes, the temperature reached 16° C. The reaction suddenly became exothermic as the temperature rose quickly within three minutes to 33° C. maximum and the solution cleared. After 30 minutes, the temperature had dropped to 26° C. GC analysis showed 38.5% cyclohexanol (CyOH), 3.7% unreacted hexenylnorbornenes, and 54.4% endo- and exo-norbornenehexanol. The reaction was stirred for additional 2.5 hrs. GC analysis showed little change in product composition. The reaction mixture was cooled to −4° C. 143.3 g 8% NaOH was added quickly within 2 minutes. The temperature rose to 6° C. The mixture was allowed to cool to +2° C. 115 ml reagent alcohol was added, causing the temperature to rise to 10° C.

The resulting hazy solution was cooled to +6° C. before adding an additional 40 ml reagent alcohol. This cleared the reaction solution. The reaction mixture was cooled further to −1° C. before adding 50 ml 35% $H_2O_2$. This addition was completed in 30 minutes, causing the temperature to rise up to 28° C. A second 57 ml portion of 35% $H_2O_2$ was added within 30 minutes, causing the temperature to rise to 30° C. After cooling to 10° C., the cooling bath was removed. The reaction mixture gradually warmed to 28° C. within 36 min. The reaction flask was placed in a water bath and allowed to stir overnight. Solids had precipitated, causing the stirrer to seize. After stirring was resumed, 20 ml concentrated HCl was added to bring the pH to ~2. The mixture was stirred and then allowed to settle. The liquid portion was decanted away from the solids and the phases were separated. The organic phase was washed with 100 ml brine, 50 ml saturated sodium bicarbonate mixed with 50 ml brine, and 2×100 ml brine to pH 7. The organic phase was then rotary evaporated from room temperature to 50° C. at 15 Torr to give 100.6 g liquid with solids. GC analysis showed 39.5% CyOH, 3.1% unreacted endo- and exo-hexenylnorbornene (HxNB), and 55.1% endo- and exo-norbornenehexanol. 100 mL deionized water was added and the mixture rotary evaporated at 55° C. and 15 Torr vacuum until all water had been removed. This left the pot with 30.9% CyOH, 3.0% endo- and exo-hexenylnorbornene, and 64.3% endo- and exo-norbornenehexanol. Azeotropic removal of CyOH and unreacted hexenylnorbornene was repeated successively with two-100 ml, one 200 ml, and two final 100-ml treatments with distilled water to give a product totaling 51.6 g which contained 0.9% CyOH, 0.8% hexenylnorbornene, and 95.9% endo- and exo-norbornenehexanol.

The mixture was initially vacuum distilled slowly through a 6.5-inch Hempel column packed with 4-inches of <7 mm i.d. glass helices. After the 4th fraction was collected, the Hempel column was replaced with a 7.5-inch Vigreux column. The total yield of CyOH-free endo-, exo-NBHxOH was 41 g (74% yield). The yield of >99% purity NBHxOH was 35.16 g (64% yield). GC analysis showed a 87:13 endo:exo ratio. NMR analysis indicated an endo:exo ratio of 79:21.

Example F5

Endo-norbornenylethanol endo-Vinylnorbornene (11.72 g, 97.48 mmol) (prepared in Example N2) was weighed and placed in a 500 mL flask inside a nitrogen purge dry-box. Anhydrous tetrahydrofuran of 200 mL was added to the flask and endo-vinylnorbornene was dissolved. To the resulting endo-vinylnorbornene solution was added dicyclohexylborane (17.41 g, 97.73 mmol) as solid by portions at room temperature. The flask was taken out from the dry-box after 3 hours of stirring at room temperature. The flask was put in an ice bath. Sodium hydroxide solution (100 ml, 3 N) was added, and then $H_2O_2$ was added slowly. The ice bath was removed and the reaction mixture warmed to 50° C. for 18 hours in an oil bath. The resulting mixture was acidified by concentrated HCl solution. Ethyl acetate was added to the mixture, and the mixture was then washed with saturated $Na_2CO_3$ and brine successively. The organic layer was dried over $MgSO_4$. Solvents were evaporated at 50° C./100 torr. DI water of 500 mL was added and the mixture was distilled at 50° C./50 torr. After evaporating the water, the distillation was continued at 60° C./2 torr. 6.23 g of endo-norbornene ethanol with 99.7% purity by GC analysis was obtained.

Example F6 exo-Norbornene-ethanol (NBEtOH)

This Example F6 illustrates formation of in situ borane, A 3-neck 500 ml flask fitted with mechanical stirrer, addition funnel, and Claisen head with nitrogen inlet and thermowell was dried with a hot air gun to 107° C. and then cooled under a nitrogen stream to ~40° C. Anhydrous diglyme (80 ml) was syringed into the flask. When the solvent had cooled to room temperature, sodium borohydride (3.3 g, 0.08 mol) was added. The mixture was stirred as cyclohexene (16.3 g, 0.2 mol) was syringed into the flask. This immediately caused the reaction mixture to sludge. The reaction mixture was cooled with an ice bath to 1° C. Dimethyl sulfate (7.6 ml, 0.08 mol) was added dropwise. Within 2 minutes, the reaction temperature had climbed to 9° C. Addition was stopped, but the reaction temperature continued to climb over the next 2 minutes to 25° C. This was accompanied by extensive foaming and evolution of methane. When the resulting white slurry had cooled to 6° C., the ice bath was replaced with a methanol-ice bath. The reaction mixture was cooled to −1° C. when addition of dimethylsulfate was resumed. Addition was completed after 10 minutes. The temperature ranged from −3° C. to −0° C. The methanol-ice bath was replaced with a water-ice bath. The reaction warmed within 3 minutes to 5° C., so the cooling bath was switched back to methanol-ice. Within 2 minutes, the temperature dropped to −8° C., so the cooling was changed back to ice-water. The reaction mixture was stirred at 0° C. for 3 hrs. Then exo-vinylnorbornene (98.3% exo, 9.6 g, 0.08 mol) was syringed into the reaction mixture at 0° C. The ice-wafer bath was removed and the reaction mixture was warmed up to 20° C. within the next 42 minutes when partial clearing of the reaction mixture occurred. After another 46 minutes at 18-23° C., the mixture was sampled. GC analysis showed a cyclohexanol:NBEtOH ratio of 59:41. Theoretical is 66:34. NMR showed no unreacted exo-vinylnorbornene remaining. The reaction mixture was stirred another 1.75 hrs at 18° C. GC analysis showed a cyclohexanol:NBEtOH ratio of 65:35. The reaction was cooled with a methanol-ice bath to −13° C. 8 wt. % aqueous NaOH (38 ml) was added within five minutes, causing the temperature to rise to 1° C. Then 33 ml of reagent alcohol was added quickly. The temperature dropped to −4° C. and the reaction mixture cleared. The reaction mixture was allowed to cool to −7° C. before adding 30 ml of 35% $H_2O_2$. The addition was completed in 13 minutes. The temperature rose to a maximum of 47° C. and then cooled back to 19° C. The reaction mixture became hazy at this point. The methanol-ice bath was removed and the reaction mixture then stirred at ambient temperature overnight. White solid had precipitated from the now clear solution. Five ml conc. HCl was added to bring the pH from 7 to 1. The reaction mixture was decanted from the solids. No phase separation occurred. The reaction flask was rinsed with ~60 ml MTBE, which in turn was used to extract the reaction mixture. The phases were separated. The acidic aqueous phase was extracted twice more with 100 ml MTBE. The MTBE extracts were combined and washed twice with 100 ml brine. The MTBE extract was washed with 50 ml saturated $NaHCO_3$ solution to pH 9 and then with 100 ml brine to pH 7. The MTBE solution was rotary evaporated up to 70° C. and 15 Torr to give 51 g liquid containing a small amount of salts. GC assay showed 43% cyclohexanol, 36% diglyme, 0.1% endo-NBEtOH, and 22% exo-NBEtOH. Cyclohexanol:NBEtOH ratio was 66:34. Yield based on GC assay was quantitative. The mixture was filtered away from the salts, rinsed with MTBE, and rotary evaporated up 90° C. and 15 Torr to give 42 g colorless liquid. GC assay was 40% cyclohexanol, 32% diglyme, 0.2% endo-NBEtOH, and 28% exo-NBEtOH. The cyclohexanol:NBEtOH ratio of 59:41 indicates some cyclohexanol and diglyme were removed by the further rotary evaporation.

Derivatization Examples

Example D1

Norborneneethylmethanesulfonate 5-(2-hydroxyethyl)norbornene (701.3 g, 5.07 mol), 4 L dichloromethane, and methanesulfonyl chloride (612.4 g, 5.34 mol) were placed in a 4-neck 12 L flask fitted with mechanical stirrer, thermowell, nitrogen inlet, and addition funnel. An extra 500 ml dichloromethane was added to rinse in the methanesulfonyl chloride. The stirred mixture was chilled to −10° C. Triethylamine (614 g, 6.03 mol) was added rapidly drop wise over a 4.5 hr period with the temperature ranging from −10 to 0° C. The resulting slurry was allowed to warm slowly to 18° C. during 2.5 hrs. Then 2 L water was added and mixed. The phases were separated and the aqueous phase extracted with 500 ml dichloromethane. The combined dichloromethane extracts were washed with 1.6 L of 1 N HCl and then washed with 2×2 L brine to a wash pH=6. The dichloromethane solution was dried over sodium sulfate, filtered, and rotary evaporated to 1196 g red liquid. NMR analysis indicated this still contained 8.6 wt. % dichloromethane. Further rotary evaporation utilizing a high vacuum pump brought the weight to 1091 g with little dichloromethane detected in the NMR. GC analysis gave mesylate content at 95.5%. The material eventually crystallized after a few weeks storage. No further purification was attempted since the material demonstrated instability during distillation.

Example D2

Exo-5-(2-Bromoethyl)norbornene

Exo-Norbornenylethylmethanesulfonate (200 g, 0.93 mol) and 2.5 L 2-pentanone were placed in a 4-neck 5 L flask fitted with mechanical stirrer, condenser, nitrogen inlet adapter, and thermowell. The mixture was stirred until ail mesylate had dissolved. Then 120.7 g (1.39 mol) lithium bromide was added. The mixture was heated to reflux, giving a white slurry. After one hour, GC analysis indicated that <0.25% starting material remained. The mixture was cooled to room temperature, filtered, the solids washed with ethyl acetate, and the filtrate rotary evaporated to give 261.2 g of liquid with solids. This residue was taken up with 250 ml dichloromethane and 200 ml water. The filtered solids were dissolved in water and extracted with dichloromethane.

The aqueous portions were combined, further diluted with water, and extracted with dichloromethane. The dichloromethane portions were combined, washed with 3×250 ml brine to clear the dichloromethane extracts and give final wash pH=5. The organic portion was dried over sodium sulfate, filtered, and rotary evaporated to give 206.1 g.

GC analysis showed 97.6% purity. Vacuum distillation through a 14-inch Vigreux column at 55° C. (1.85 Torr)-58° C. (1.80 Torr) yielded 154.5 g (83% yield). GC analysis showed >98.8% purity. An additional 16.3 g of very yellow fore- and post-run were also collected, both showing >98.5% purity.

Example D3

Exo-5-(2-Iodoethyl)norbornene (Exo-NBEtI)

Exo-Norborneneethylmethanesulfonate (200 g, 0.925 mol) and 2.5 L 2-pentanone were placed in a 4-neck 5 L flask fitted with mechanical stirrer, condenser, nitrogen inlet adapter, and thermowell. The mixture was stirred until all mesylate had dissolved. Then 209 g (1.39 mol) sodium iodide was added. The resulting slurry was heated to reflux. At 64-70° C., the mixture became very thick, so an additional 500 ml 2-pentanone was added and the stir rate was increased. GC analysis indicated that <0.24% starting material remained upon reaching reflux (100° C.). The mixture was refluxed for 70 minutes and then cooled to room temperature. The mixture was tediously filtered as the fine solids plugged the filter. The filtrate was rotary evaporated until solids precipitated out. This was treated with 150 ml water. The filtered solids were dissolved in water, the layers separated, and the remaining aqueous phase extracted with 2×150 ml ethyl acetate. The ethyl acetate extracts were added to the rotary evaporator residue and the phases separated. The organic portion was washed and decolorized with 250 ml 10% aqueous sodium bisulfite, and then washed with 250 ml brine, 100 ml saturated sodium bicarbonate, 250 ml brine, and 100 ml deionized water (final wash pH=8). The organic portion was dried over sodium sulfate overnight, filtered, and rotary evaporated to yield 231.6 g light brown liquid. GC analysis indicated 97.3% purity.

Vacuum distillation through a 14-inch Vigreux column gave:

1. 70.2° C. (1.75 Torr)-69.6° C. (1.70 Torr), 31.72 g, yellow, 97.2% purity
2. 70.5° C. (1.75 Torr)-69.5° C. (1.60 Torr), 172.46 g, light yellow, 99.6% purity
3. 69.4° C. (1.65 Torr)-76.6° C. (1.75 Torr), 10.18 g, brown, 97.8% purity.

Fraction 3 was diluted with 25 ml dichloromethane, washed and decolorized with 25 ml 10% aqueous sodium bisulfite, and then washed with 25 ml brine, 10 ml saturated sodium bicarbonate, and another 25 ml brine. After drying over sodium sulfate, the fraction 3 solution was combined with fraction 1 and redistilled to give at 70.1° C. (1.75 Torr)-69.8° C. (1.70 Torr) 26 g of pale yellow liquid, 98.8% purity. Total yield was 199 g (86% of theoretical).

Example B4

Endo-,exo-norbornenylhexyloxymethyl-1,1,1,3,3-hexafluoro-2-propanol (NBHMHFP)

NaH (60%, 10.86 g, 0.271 mol) was placed in a 4-neck 500-ml flask fitted with mechanical stirrer, addition funnel, thermowell, and condenser with nitrogen gas inlet. 110 ml dry THF was added and stirring commenced. The resulting slurry was mechanically stirred while cooling to −8° C. Endo-/exo-NBHxOH (fractions 5+6, >99.2%, 37.68 g, 0.194 mol) was dissolved in 25 ml dry THF and added rapidly drop wise to the NaH/THF mixture. Addition time was 3 min with the temperature ranging from −8° C. to −3° C. Vigorous bubbling occurred. When the temperature dropped to −7° C., the cooling bath was removed and the reaction was allowed to warm to room temperature. Another 0.81 g NaH (60%, 0.02 mol) was added. The mixture was allowed to stir overnight. The reaction was cooled to −14° C. and 35.2 g (0.196 mol) hexafluoroisobutylene epoxide (HFIBO) was added rapidly drop wise. Addition time was 2 minutes with the temperature ranging from −14° C. to −4° C. After cooling to −9° C., the cooling bath was removed and the mixture was allowed to warm. After one hour, the temperature reached 41° C. and a gentle reflux was observed. After another 90 minutes, the reaction had cooled to 26° C. GC analysis showed 2.7% unreacted endo-,exo-NBHxOH and 96.8% endo-/exo-NBH-MHFP. After another 4 hours, GC analysis showed 0.6% unreacted endo-/exo-NBHxOH and 99% endo-/exo-NBHM-HFP. The mixture was stirred overnight. GC analysis showed 0.3% unreacted endo-,exo-NBHxOH and 98.8% endo-/exo-NBHMHFP. The mixture was cooled to −8° C. and quenched with 7 ml water. Quench time was 3 minutes with the temperature rising to +5° C. When the temperature began to drop, the cooling bath was removed and the mixture rotary evaporated to ~88 g of yellow oil. This was taken up with 100 ml cyclohexane, heated, allowed to settle, and the cyclohexane decanted. The residue was heated with another 150 ml cyclohexane, allowed to settle, and the cyclohexane decanted, GC analysis of remaining brown oil gave very weak signals for both starting material and product, suggesting the oil was mainly NaOH. The cyclohexane extracts were rotary evaporated to give 78.4 g of a yellow oil. GC analysis showed 0.3% NBHxOH, 98.95 NBHMHFP, and 0.6% suspected bis-adduct. The oil was mixed with 100 ml pentane to give murky, yellow liquid which gradually precipitated a brown oil. The pentane solution was decanted from the brown oil and then mixed with 400 ml deionized water to give a milky liquid with pH=14. No phase separation occurred and attempts to concentrate the mixture by rotary evaporation were thwarted by excessive foaming. The mixture was transferred to a separatory funnel via generous washings with water (until the water wash measure to a pH=7). Total volume was 700 ml. The mixture was acidified with 50 ml concentrated HCl. The murky, pale yellow liquid that separated as the lower phase was collected, giving 66.9 g of the product (99% crude yield). GC analysis showed 0.3% NBHxOH, 99% NBHMHFB, and 0.6% suspected bis-adduct. The product was diluted with 100 ml dichloromethane, washed with 2×50 ml 3.5N aqueous HCl, washed with 3×100 ml and with 200 ml brine. An emulsion formed at the interface of the last wash. The dichloromethane phase was separated and 100 ml water added to the remaining phase. After mixing gently, additional organic phase separated and was drained. The aqueous phase had pH=6. The dichloromethane portions were combined, dried over sodium sulfate, filtered when clear, and rotary evaporated to obtain 64.6 g clear yellow liquid. GC analysis showed 0.2% NBHxOH, 98.9% NBHMHFB, and 0.8% bis adduct. Endo:exo ratio was 80:20 by NMR analysis. Distillation of the product through a 6-inch Vigreux column was attempted, but the vapors could only get ~⅓ of the way up the column when heating with a 151° C. oil bath at 1.10 Torr. The Vigreux column was removed and distillation continued to give 41.18 g of product with a >98% from 6 fractions.

The final residue, totaling 15.8 g, contained 91% NBHM-HFB. The residue was distilled in the Kugelrohr oven at 138° C. (0.89-0.92 Torr) to collect 15 g of the purified product. GC analysis showed 98.3% NBHMHFB. This was distilled again in the Kugelrohr oven at 130° C. (0.90-1.05 Torr) to 8.76 g for which GC analysis showed 99.5% NBHMHFB, 0.5% bis adduct, and no NBHxOH.

Example D5

Exo-norbornene-3-propionic acid

A 4-neck 3-L flask fitted with mechanical stirrer, addition funnel, thermowell, and Claisen head holding a second addition funnel and condenser (with nitrogen inlet adapter) was dried at ~110° C. under a nitrogen flush. When cooled to room temperature, magnesium turnings (18.4 g, 0.765 mol) were placed in the flask, followed by 100 ml DrySolve THF from one of the addition funnels. A solution of 5-(1-bromoethyl)-norbornene (148 g, 0.736 mol) in 350 ml DrySolve THF was added from the 2nd addition funnel. After four minutes, the temperature rose from 20 to 22° C. rapidly. 785 ml of THF was added from the 1st addition funnel immediately. The temperature had risen to 27° C. when the THF addition was completed. When the temperature reached 41° C., addition of the bromoethylnorbornene was stopped. The temperature climbed to 55° C. so another 100 ml of DrySolve THF was added. The temperature maximized at 56° C. before self-cooling. At 42° C., addition of the bromoethylnorbornene recommenced. Addition of bromoethylnorbornene continued until the temperature reached 50° C., then stopped, and resumed again upon cooling to 39° C. This was repeated until all bromoethylnorbornene had been added. Total addition time was 2 h 20 min. The mixture was allowed to stir 2 h while cooling back to room temperature. GC analysis indicated no starting material remaining. The Grignard reagent was cooled to −70° C. before bubbling carbon dioxide below the surface of the liquid. The reaction warmed to −21° C. before self-cooling to −60° C. when addition of $CO_2$ was stopped. The mixture was allowed to warm to −10° C. GC analysis indicated 7% unreacted Grignard reagent remained. Additional $CO_2$ was bubbled into the mixture for nine minutes between −2 to 0° C. GC analysis still indicated 7% unreacted Grignard reagent. The reaction was allowed to warm and stir overnight. GC analysis again showed 7.5% unreacted Grignard reagent (analyzed as ethylnorbornene). The reaction was cooled to −15° C. before adding 7.50 ml of 18% aqueous HCl rapidly, which caused the temperature to rise to −2° C. The mixture was extracted with 250 ml dichloromethane, giving an upper organic phase. After separating the phases, the aqueous phase was extracted with 6×250 ml dichloromethane. The organic portions were combined and concentrated via rotary evaporation to 125.3 g brown liquid and solids. This was dissolved in 250 ml dichloromethane and treated with 250 ml of 8% aqueous sodium hydroxide. The organic phase was again on top, pH of the aqueous phase was only 7, so the organic portion was extracted again with 250 ml 8% aqueous sodium hydroxide. The resulting emulsion was treated with 200 ml distilled water and 250 ml dichloromethane to help phase separation. The aqueous base extracts were washed with 4×250 ml dichloromethane, giving slow separating phases. The base extracts were washed with 2×250 ml cyclohexane, giving better separation. The base extracts were acidified with 100 ml concentrated HCl to pH 2. A small amount of product separated and was collected. The aqueous phase was extracted with 3×250 ml dichloromethane. The organic portions were combined, washed with 500 ml brine to pH 6, and then dried over sodium sulfate. The product solution was filtered and rotary evaporated to 88.75 g (72% yield) yellow oil. GC analysis gave 91% purity. NMR analysis indicated the product contained 4.8 wt. % dichloromethane.

Example D6

Exo-norbornene-3-propionic acid ethyl ester

Exo-norbornene-2-propionic acid (94.22 g, 0.567 mol) was mixed with 250 ml absolute alcohol and 5.2 ml of concentrated sulfuric acid. The solution was heated to gentle reflux for three hours, when GC analysis confirmed the reaction was complete (note: the reaction was complete after one hour, but similarity of starting material and product GC retention times delayed confirmation of this). The solution was cooled to below room temperature and poured into 1 L distilled water. A yellow product phase separated from the milky aqueous portion. The aqueous phase is extracted with 2×250 ml dichloromethane. The organics were combined and washed with 250 ml saturated sodium bicarbonate. This gave very slow separating phases. The interface was set aside while the organic portion was washed with 250 ml brine to pH 7. Again, phase separation was slow. The interface was segregated and set aside. The organic portion was dried over sodium sulfate, filtered, and rotary evaporated to give 109.6 g. GC analysis showed 84.6% purity. The product was vacuum distilled through a 14-inch Vigreux column to give 77.48 g of >99% pure ester for a 70% yield.

Example D7

Exo-Norborneneethylhexafluoroalcohol (Exo-HFAENB)

A 3 L 4-neck flask fitted with mechanical stirrer, dry ice condenser, thermowell, and two-way adapter fitted with septa and nitrogen inlet was heated and hot air-dried to ~120° C. under nitrogen flush. After cooling to room temperature, zinc dust (Alfa-Aesar A13633, 107.9 g, 1.65 mol) was placed in the flask, followed by 1 L Dry Solve dimethylacetamide (DMA). The mixture was stirred as iodine (27.9 g, 0.11 mol) was added. The mixture warmed to 29° C. and initially turned yellow. After 1 minute, the zinc slurry had turned back to gray. After waiting an additional six minutes, exo-NBEtBr (223 g, 1.1 mol) was added all at once. The mixture was heated to 80° C. Upon reaching 81° C., the temperature suddenly climbed to 112° C. before subsiding after the heating source had been removed. When the temperature dropped back to 89° C., the heat source was returned. After 1 hour, GC analysis showed no NBEtBr remaining. The mixture was stirred an additional 14 min at 80° C. before cooling to −29° C. in an acetonitrile/dry ice cooling bath. Hexafluoroacetone (HFA) (201.3 g, 1.21 mol) was condensed into the reaction mixture. The temperature ranged from −31 to −14° C. during the 17 minute addition time. The cooling bath was replaced with an isopropanol/water/dry ice cooling bath. The reaction mixture was stirred at −16 to −2° C. for 5.5 hours when GC analysis indicated that the HFAENB to NBEt (from hydrolyzed NBEtZnI) signal ratio had become constant and no longer increasing. The mixture was chilled to −33° C. before adding distilled water carefully in 100 to 250 ml increments up to a total water volume of 1500 ml. The quenched mixture was poured into 2000 ml distilled water. The reaction flask, containing considerable Zn sludge, was rinsed with 2×250 ml water and 2×250 ml and 200 ml 3.5 N HCl. The rinsing was combined with the aqueous quench mixture. The combined aqueous mixture was extracted with 3×1.3 L cyclohexane. The cyclohexane extracts were washed with 1 L brine to pH 6. The cyclohexane extracts were filtered and then treated successively with 400 ml and 200 ml 25% aqueous TMAOH, GC analysis indicated that no HFAENB remained in the cyclohexane phase. The TMAOH extracts were combined and washed with 3×100 ml cyclohexane. The aqueous phase was acidified with 200 ml concentrated HCl. A lower phase totaling 383.1 g of >91% HFAENB separated out but still contained 12.2 wt. % DMA. The HFAENB was diluted with ~400 ml dichloromethane and then washed with 3×400 ml 31.5% sulfuric acid. The organic phase became the upper layer. NMR analysis showed no significant DMA signals remaining in the organic phase. The dichloromethane solution was washed with 500 ml brine to pH <2, and then with 100 ml saturated sodium bicarbonate mixed with 150 ml brine. A slow separating emulsion resulted. Additional 250 ml brine was added and the organic phase that separated was removed. The aqueous phase was treated successively with 5×10 ml 3.5N HCl to bring the pH from 9 to 6. The organic phase that separated was removed and combined with the previous organic phase. The combined organic phase was washed with 250 ml brine to pH 6 and then dried over sodium sulfate overnight. The solution was filtered and rotary evaporated to 299.5 g (94.4% yield), GC analysis showed 99.4% purity. The crude product was vacuum distilled through a 12-inch Vigreux column. Fractions II and III were combined to give 258.2 g (81% yield). This lot showed trace or no HFA signal at −70.7 ppm in the $^{19}$F NMR and no DMA by proton NMR.

Example D8

Synthesis of exo-NBEtPh

Under a nitrogen atmosphere, to a THF (4.0 mL) solution of exo-vinylnorbornene (0.25 g, 2.1 mmol) at 0° C., was added slowly a THF solution of dicyclohexylborane (4.2 mL 0.5 M). The reaction was allowed to warm room temperature and stirred for 16 hours. Dimethylformamide (16.0 mL), [1,1'-bis(diphenylphosphino)ferrocene]dichloropalladium (II) (42 mg, 0.058 mmol), iodobenzene (0.39 g, 1.9 mmol) and potassium carbonate (0.52 g, 3.8 mmol) were added to the reaction mixture. The reaction was refluxed for 72 hours. The reaction mixture was extracted with ethyl acetate and washed with water. The organic layer was dried over magnesium sulfate and evaporated solvents. Formation of exo-NBEtPh was confirmed by GC-MS analysis of the crude product.

Example C1-C12

Syntheses of
Norbornenylhydrocarbylene-diorganoboranes

C1. Addition of 9-Borabicyclo[3.3.1]nonane to exo-Vinylnorbornene

To a stirred THF (2 ml) solution of 1,5-cyclooctadiene (0.22 g, 2 mmol) at 0° C., was added a THF solution of Me$_2$S.BH$_3$ (1 ml of a 2 M THF solution). The reaction was allowed to proceed for 3 h at 0° C., at which point the borane was added to a THF (2 ml) solution of exo-vinylnorbornene (0.24 g, 2 mmol) and 1,2-dimethoxybenzene (veratrole) (0.28 g, 2 mmol, used as an internal standard). The reaction mixture was allowed to warm to room temperature over a period of 18 h at which point solvent was removed under vacuum and resulted in a colorless oil. The structure was confirmed by $^1$H and $^{11}$B NMR spectroscopy.

C2. Addition of Di(2-methylcyclopentyl)borane to exo-Vinylnorbornene

Example C1 was substantially repeated except for using 1-methyl-1-cyclopentene (0.33 g, 4 mmol) instead of 1,5-cyclooctadiene in this Example C2. The reaction mixture was allowed to warm to room temperature over a period of 2 h at which point solvent was removed under vacuum and resulted in a colorless oil. The structure was confirmed by $^1$H and $^{11}$B NMR spectroscopy.

C3. Addition of Dicyclooctylborane to exo-Vinylnorbornene

Example C1 was substantially repeated except for using cis-cyclooctene (0.44 g, 4 mmol) instead of 1,5-cyclooctadiene in this Example C3. The structure was confirmed by $^1$H and $^{11}$B NMR spectroscopy.

C4. Addition of Dicyclopentylborane to exo-Vinylnorbornene

Example C1 was substantially repeated except for using cyclopentene (0.27 mg, 4 mmol) instead of 1,5-cyclooctadiene in this Example C4. The structure was confirmed by $^1$H and $^{11}$B NMR spectroscopy.

C5. Addition of Di(isopropylprenyl)borane to exo-Vinylnorbornene

Example C1 was substantially repeated except for using 2,5-dimethylhexa-2,4-diene (0.55 g, 5 mmol) instead of 1,5-cyclooctadiene in this Example C5. The structure was confirmed by $^1$H and $^{11}$B NMR spectroscopy.

C6. Addition of Disiamylborane to exo-Vinylnorbornene

Example C1 was substantially repeated except for using 2-methyl-2-butene (2 mL of a 2 M THF solution) instead of 1,5-cyclooctadiene in this Example C6. The structure was confirmed by $^1$H and $^{11}$B NMR spectroscopy.

C7. Addition of Bis(3,6-dimethylcyclohexyl)borane to exo-Vinylnorbornene

Example C1 was substantially repeated except for using 3,6-dimethylcyclohexene (0.43 g, 4 mmol) instead of 1,5-cyclooctadiene in this Example C7. The structure was confirmed by $^1$H and $^{11}$B NMR spectroscopy.

C8. Addition of Di(2-methylcyclohexyl)borane to exo-Vinylnorbornene

Example C1 was substantially repeated except for using 2-methylcyclohexene (0.39 g, 4 mmol) instead of 1,5-cyclooctadiene in this Example C8. The structure was confirmed by $^1$H and $^{11}$B NMR spectroscopy.

C9. Addition of Dicyclohexylborane to exo-Vinylnorbornene

Under an atmosphere of nitrogen, dicyclohexylborane dimer (267 mg, 0.75 mmol) was added as a solid to a stirred toluene (5 mL) solution of exo-vinylnorbornene (200 mg, 1.67 mmol). The solution became clear upon addition of the borane and the reaction was allowed to proceed for 1 hour at RT. Removal of the solvent under vacuum afforded a colorless oil. The structure was confirmed by $^1$H and $^{13}$C NMR spectroscopy.

C10. Addition of Di(isopinocampheyl)borane to exo-Vinylnorbornene

Example C1 was substantially repeated except for using α-pinene (0.55 g, 4 mmol) instead of 1,5-cyclooctadiene in this Example C10. The structure was confirmed by $^1$H and $^{11}$B NMR spectroscopy.

C11. Addition of Bis(3,5-dimethylcyclopentyl)borane to exo-Vinylnorbornene

Example C1 was substantially repeated except for using 3,5-dimethylcyclopentene (0.19 g, 2 mmol) instead of 1,5-cyclooctadiene, a THF solution of Me$_2$S.BH$_3$ (0.5 mL of a 2 M THF solution), a THF (2 ml) solution of exo-vinylnorbornene (0.12 g, 1 mmol) and veratrole (0.14 g, 1 mmol, used as an internal standard) in this Example C11. The structure was confirmed by $^1$H and $^{11}$B NMR spectroscopy.

C12. Addition of Dimesitylborane to exo-Vinylnorbornene

Dimesitylborane (500 mg, 1 mmol) was added as a solid to a stirred THF (2 ml) solution of exo-vinylnorbornene (300 mg, 2.5 mmol). The solution became clear upon addition of the borane and the reaction was allowed to proceed for 48 h at RT. Removal of the solvent under vacuum afforded a colorless oil. Isolated yield from hexane: 76%. Single crystals suitable for X-ray analysis were obtained from a saturated hexane solution stored at −30° C. The structure was confirmed by $^1$H and $^{13}$C NMR spectroscopy and X-ray crystallography. FIG. 1 shows an Oak Ridge Thermal Ellipsoid Plot (ORTEP) diagram of exo-NBCH$_2$CH$_2$B(mesityl)$_2$) such as made by the method of Example C12.

Example 1

Syntheses of Norbornenylhydrocarbylene-diorganoboranes from Various Diorganoboranes and VinylNB Various diorganoboranes of Formula A as described herein were selectively reacted with vinylnorbornene. The regiochemical selectivity of the resulting compounds along with the observed $^{11}$B NMR chemical shifts of the dimeric or the monomeric forms of the organoboranes and the measured single crystal C—B—C bond angles are summarized in Table 7. It is apparent form this data that 100 percent regiochemical selectivity for vinyl addition was observed when the C—B—C bond angle is greater than 119°. In comparison 9-BBN with a C—B—C bond angle of 111.6° exhibits only 70 percent selectivity to vinyl addition product.

It is also evident that Lewis base adduct of a diorganoborane can achieve high regiochemical selectivity as presented in Table 7 especially when the parent borane has a C—B—C bond angle greater than 120°. For instance, dicyclohexylborane-2-picoline (1:1) exhibits 100 percent selectivity at the vinyl group, wherein the parent diorganoborane has a C—B—C bond angle of 120°.

During the course of our investigations, it was noted that the preparation of certain dihydrocarbylboranes, i.e., (o-tolyl)$_2$BH and (2-MeCp)$_2$BH, were more difficult than others to isolate in pure form based on method of preparation and we believe that certain diorganoboranes were more prone to redistribution via rearrangement by boron-H exchange throughout the hydrocarbon skeleton which results in the boron at bonded on terminal carbon atom as shown in previously presented Schemes 1a and 1b than other dihydrocarbylboranes. Thus this redistribution may be the cause of the dihydrocarbylborane (2-MeCp)$_2$BH showing lower regiostereochemical selectivity than its analog Cp$_2$BH and the negative effects of such redistribution is likely to be controllable by contacting the vinylnorbornene with the dihydrocarbylborane at a temperature where such redistribution is reduced.

We also believe that there are methods which can be employed to generate these materials in pure form via the methods developed by H. C. Brown and S. K. Gupta, *Journal of Organometallic Chemistry* 156:95-99 (1978).

TABLE 7

Syntheses of Norbornenylhydrocarbylene-diorganoboranes from Various Diorganoboranes and VinylNB

| Diorganoborane | $^{11}$B NMR Dimeric [R$_2$BH]$_2$ ppm (solvent) | $^{11}$B NMR Monomeric R$_2$BH ppm (solvent) | C-B-C Angle (°) | Regiochemical Selectivity of Vinyl:NB (before purification) |
|---|---|---|---|---|
| 9-BBN | 27.6 (toluene) 28.0 (THF) | | 111.6 111.8 | 70:30 |
| (o-tolyl)$_2$BH | | | | 57:43 |
| (2-MeCp)$_2$BH | | | | 70:30 |
| (Cyclooetyl)$_2$BH | | | | 75:25 |
| 3,6-dimethylborepane | | | | 94:6 |
| Cp$_2$BH | | | | 95:5 |
| (Siamyl)$_2$BH | 30.0 (THF) | | | 95:5 |
| (3,6-Me$_2$Cy)$_2$BH | | | | 96:4 |
| (2-MeCy)$_2$BH | | | | 99:1 |
| (Isopropylprenyl)$_2$BH | | | | 100:0 |
| Cy$_2$BH | 30.5 (Et$_2$O) | | 119.0 | 100:0 |
| Di(isopinocampheyl)borane | 38.3 (unknown) | | 126.7 | 100:0 |
| (3,5-Me$_2$Cp)$_2$BH | | | | 100:0 |
| (Mesityl)$_2$BH | 25.9 (unknown) | 84.3 (unknown) | 123.2 | 100:0 |
| (Tri(isopropyl)phenyl))$_2$BH | | 73.5 (unknown) | 128.0 | 100:0 |
| Dicyclohexylborane-2-picoline (1:1) | | | | 100:0 |

Example 2

Thermochemical Calculations and Observed Experimental Values for the Hydroboration Reactions The ab-initio calculations were performed using the Gamess 09, NWchem and Gaussian software packages. Reactants, products and transition states for the reaction of organoborane compounds of Formula A with exo-vinylnorbornene were optimized at the B3LYP/6-311+G level of theory. C—B—C bond angles of organoborane compounds of Formula A correspond to geometries optimized at this level. The measured and calculated C—B—C bond angles are summarized in Table 8. Equilibrium and transition state geometries were confirmed by the presence of exactly zero and one imaginary frequency, respectively, in the subsequent vibrational analysis. Enthalpies and free energies (at 298K) of optimized structures in the series were estimated from frequency calculations (B3LYP/6-311+G) using the harmonic oscillator and rigid rotor approximations. Estimates of vinyl addition selectivity ($k_{NB}/k_{vinyl}$) were made by comparison of calculated gas phase free energies ($\Delta G^{\ddagger}_{298K}$) for the ring and vinyl addition transition states using the relation: $k_{NB}/k_{vinyl}=e^{-\Delta\Delta G\ddagger/RT}$. Selectivities derived from calculated gas phase enthalpies and free energies of activation were found to be in qualitative agreement with results observed in solution as summarized in Table 8. Using the model defined above it is now calculated that with gas phase selectivities of $k_{NB}/k_{vinyl} \leq 0.1$ results in greater than 90% selectivity for vinyl addition.

TABLE 8

Calculated (B3LYP/6-311 + G**) C-B-C Bond Angles of Dialkylboranes

| Borane | Calculated | Measured | Predicted % Vinyl Selectivity |
|---|---|---|---|
| 3344Me₄Borolane | 107.6 | | 66.1 |
| Borolane | 107.7 | | 69.9 |
| MeBorolane | 108.4 | | 92.1 |
| 25Me₂Borolane | 109.1 | | 99.9 |
| 2255Me₄Borolane | 110.1 | | 99.9 |
| 9-BBN | 112.3 | 111.8[a] | 97.8 |
| 35Me₂Borinane | 120 | | 98.9 |
| Borinane | 120.2 | | 99.3 |
| MeBorinane | 121 | | 99.4 |
| Me₂Borinane | 121.4 | | 99.5 |
| Et₂BH | 122.5 | | 99.8 |
| iProp₂BH | 123.7 | | 99.3 |
| Me₂BH | 125.1 | | 99.2 |
| Cp₂BH | 125.7 | | 99.8 |
| (2MeCp)₂BH | 126.2 | | 99.8 |
| Cy₂BH | 126.5 | 119.0[b] | 100 |
| Borepane | 126.6 | | 99.3 |
| Ph₂BH | 126.9 | | 97.6 |
| Me₂Borepane | 127.5 | | 99.5 |
| diippBH | 127.8 | | 100 |
| (26Me₂Ar)₂BH | 128.4 | | 100 |

[a]Brauer, D. J. & Kruger, C. (1973) Acta Cryst. B29, 1684-1690 and S.Sabo-Etienne Journal of Organometallic Chemistry 680 (2003) 182-187.
[b]Richard Mynott et al. Chem, Ear, J. 2007, 13, 8762-8783.

Based on the calculated C—B—C bond angle model as summarized in Table 8 the diorganoboranes having a C—B—C bond angle of greater than or equal to 120° affords a vinyl addition selectivity of at least 97.6 percent. It is further observed that a borane having a C—B—C bond angle greater than 127.5° affords a vinyl addition selectivity of at least 99.5 percent. Therefore this model can be used as a basis to select a suitable diorganoborane compound, which can be further optimized using other methods as further described herein below, e.g., kinetic measurements monitored by ¹H NMR.

Further evidence for the selectivity of a desired borane compound of Formula A can be obtained from the B3LYP/6-311+G** gas phase geometries of the boranes of Formula A, $(R^1)(R^2)BH$. Despite the wide variety of substituents that can be employed in compounds of Formula A, such as 9BBN, boralane 3344Me4Borolane where steric interaction in the hydroboration reaction is significantly attenuated by geometric constraints, the observed selectivities of these compounds is comparatively low. The boranes of this class are identified as having markedly decreased C—B—C bond angles. It has now been found that the boranes of Formula A with C—B—C angles of greater than 120 degrees are, in general, suitable reagents for the desired selectivity for vinyl addition.

The data obtained in these free energy calculations, $\Delta\Delta G^{\ddagger}$, which is a difference between the free energies of the transition state of the addition of the borane to an internal ring double bond and the transition state of the vinyl addition are summarized in Table 9. Also summarized are the observed selectivities to the vinyl addition product as well as the calculated or the predicted selectivity from the above calculations. It is quite apparent from this data that the calculated values are very much in agreement with the observed values. Thus, this model is very useful in predicting the selectivity of the vinyl addition product.

TABLE 9

Summary of Observed and Calculated Thermochemical Values

| Borane | $\Delta\Delta G^{\ddagger}$ in kcal/mol | % vinyl addition (experimental) | % vinyl addition (predicted) |
|---|---|---|---|
| diippBH | 7.0 | 100 | 100 |
| (26Me₂Ar)2BH | 6.0 | | 100 |
| Cy₂BH | 4.6 | 100 | 100 |
| Me₂Borinane | 4.5 | | 99.9 |
| 2255Me₄Borolane | 3.9 | | 99.9 |
| Et₂BH | 3.8 | | 99.8 |
| Me₂Borepane | 3.1 | 94 | 99.5 |
| MeBorinane | 3.0 | | 99.4 |
| Borinane | 3.0 | | 99.3 |
| Borepane | 2.9 | | 99.3 |
| iProp₂BH | 2.9 | | 99.3 |
| Me₂BH | 2.9 | | 99.2 |
| 9BBN | 2.2 | 70 | 97.8 |
| Ph₂BH | 2.2 | | 97.6 |
| Borolane | 0.5 | | 69.9 |
| 3344Me₄Borolane | 0.4 | | 66.1 |
| BH₃ | −0.1 | 50 | 46.1 |
| MeBorolane | 1.5 | | 92.1 |
| Cp₂BH | 5.8 | 95 | 99.8 |
| 34Me₂Borolane | 0.4 | | 66.1 |
| 35Me₂Borinane | 4.5 | | 98.9 |
| 25Me₂Borolane | 3.9 | | 99.9 |
| (2MeCp)₂BH | 3.7 | 97 | 99.8 |
| CyOct₂BH | 5.1 | 85 | 100 |
| (35Me₂Cy)₂BH | | 100 | |
| (2MeCy)₂BH | | 99 | |
| (25Me₂Cy)₂BH | | 96 | |
| NB₂BH | | 80 | |
| (siamyl)₂BH | | 95 | |
| (o-tolyl)₂BH | | 57 | |

Example 3

NMR Measurements Hydroboration Reactions of 5-vinyl-2-norbornene

The room temperature $k_{NB}/k_{vinyl}$ values for the addition of Cy₂BH, 9BBN and BH₃ to exo-vinylnorbornene were measured by ¹H NMR in tetrahydrofuran. The obtained experimental data was fit using a second order irreversible model where all reagents are in their monomeric form (i.e., $(R^1)(R^2)$ BH or THF:$(R^1)(R^2)$BH). These $k_{NB}/k_{vinyl}$ values were compared to the corresponding ab initio calculations and the experimental reaction selectivities obtained from GC measurements. Mole fractions and percent conversions of the vinyl and NB addition products can be calculated using the relation: [NB]/[vinyl]=$k_{NB}/k_{vinyl}$. The measured solution phase selectivities of $k_{NB}/k_{vinyl} \leq 0.01$ of a series of borane compounds of Formula A were found to exhibit greater than 99% selectivity for vinyl addition. A representative data from these calculations are summarized in Table 10.

TABLE 10

| Reagent | $k_{NB}/k_{vinyl}$ |
|---|---|
| $BH_3$ | 1.02 |
| 9-BBN | 0.58 |
| $Cy_2BH$ | <0.01 |

It is clear from the data summarized in Table 10 that $BH_3$ and 9-BBN are non-selective to the vinyl addition. On the other hand, it has now been found that $Cy_2BH$ provides greater than 99 percent selectivity to vinyl addition ($k_{NB}/k_{vinyl}$=0.01 means 99 percent vinyl selectivity). Regarding the suitable selection of diorganoborane one skilled in the art would be able to apply $^1H$ NMR kinetic measurements to verify the selectivity of the proposed diorganoborane (see Example 4).

Further insight into the degree of steric influence of substituent groups, $R^1$ and $R^2$ can be gained from the $^{11}B$ chemical shift of Lewis pairs (relative to $BF_3:Et_2O$). $^{11}B$ Chemical shifts of pyridine adducts $Cy_2BH$, 9-BBN, and $BH_3$ were plotted against their observed selectivities in tetrahydrofuran. Data were found to fit the relation: % vinyl addition=2.87* ($^{11}B$ Chemical Shift)+80.6. Thus, pyridine adducts of ($R^1$)($R^2$)BH with chemical shifts of 5 ppm and greater, in general, are suitable boranes to be employed for achieving the desired selectivity for vinyl addition.

Example 4

Kinetic Measurements by NMR

Preparation of Stock Solutions and Time Zero Measurements:

In a typical procedure exo-vinylnorbornene (0.12 g, 1.0 mmol) and benzene (10 µl, 0.1 mmol for internal standard in $^1H$ NMR spectra) were dissolved in THF-d8 under inert atmosphere and sealed in a vial. A 0.8 ml aliquot of the solution was removed from the vial and sealed in an NMR tube under inert atmosphere. $^1H$ NMR spectra of the sample were recorded at −30, −20, −10, 0 and 10° C. for time=0 measurements of the subsequent reactions at these temperatures. A separate stock solution of borane was prepared by dissolving the borane (0.20-0.30 g, 1.0-8.0 mmol) in 5.0 ml THF. For reactions involving $BH_3$.THF the reagent was purchased from a chemical supplier as a 1.0 M stock solution and absolute purity/concentration was determined by $^{11}B$ NMR analysis of standard additions of a lithium tetrakis[perfluorophenyl]borate solution of known concentration.

$^1H$ NMR Measurements of Reaction Kinetics:

A small portion (1-4 ml, 1.0-6.5 mmol) of the borane stock was added to an NMR tube under inert atmosphere. The tube was then placed in a constant temperature bath for several minutes in order to ensure that thermal equilibrium had been established. At this time a small (0.1-1.0 ml, 0.2-2.0 mmol) portion of exo-vinylnorbornene stock was removed from the vial and added to the reaction vessel under inert atmosphere while submerged in a constant temperature bath. After agitation/mixing of the NMR tube for 1-2 minutes at this temperature the NMR tube was transferred to the spectrometer. A series of $^1H$ NMR spectrum were recorded over time at the same temperature as the constant temperature bath used during injection of the borane reagent. $^1H$ NMR measurements of $BH_3$.THF reactions incorporated a WET (Water suppression Enhanced through T1 effects) solvent suppression sequence and appropriate corrections to the relative integration as determined by experiments with various mixtures of exo-vinylnorbornene and an internal standard of known stoichiometry and concentration. Loss of the olefinic protons of exo-vinylnorbornene and appearance/disappearance of the olefin signals of the transient vinyl and ring single addition products were simultaneously fit to a second order irreversible model.

By now it should be realized that methods of identifying dihydrocarbylboranes that can exhibit enhanced regiostereochemical selectivity when reacting with an alkenylnorbornene, represented by Formula B, have been disclosed herein, such methods providing means for obtaining desired norbornenylhydrocarbylene dihydrocarbylboranes, represented by Formula (I), having high purity. That is to say regiostereochemical purities of at least 90% for some such embodiments of the present invention and for other embodiments, regiostereochemical purities of at least 95% and for still others regiostereochemical purities of at least 99%.

Figure 2:
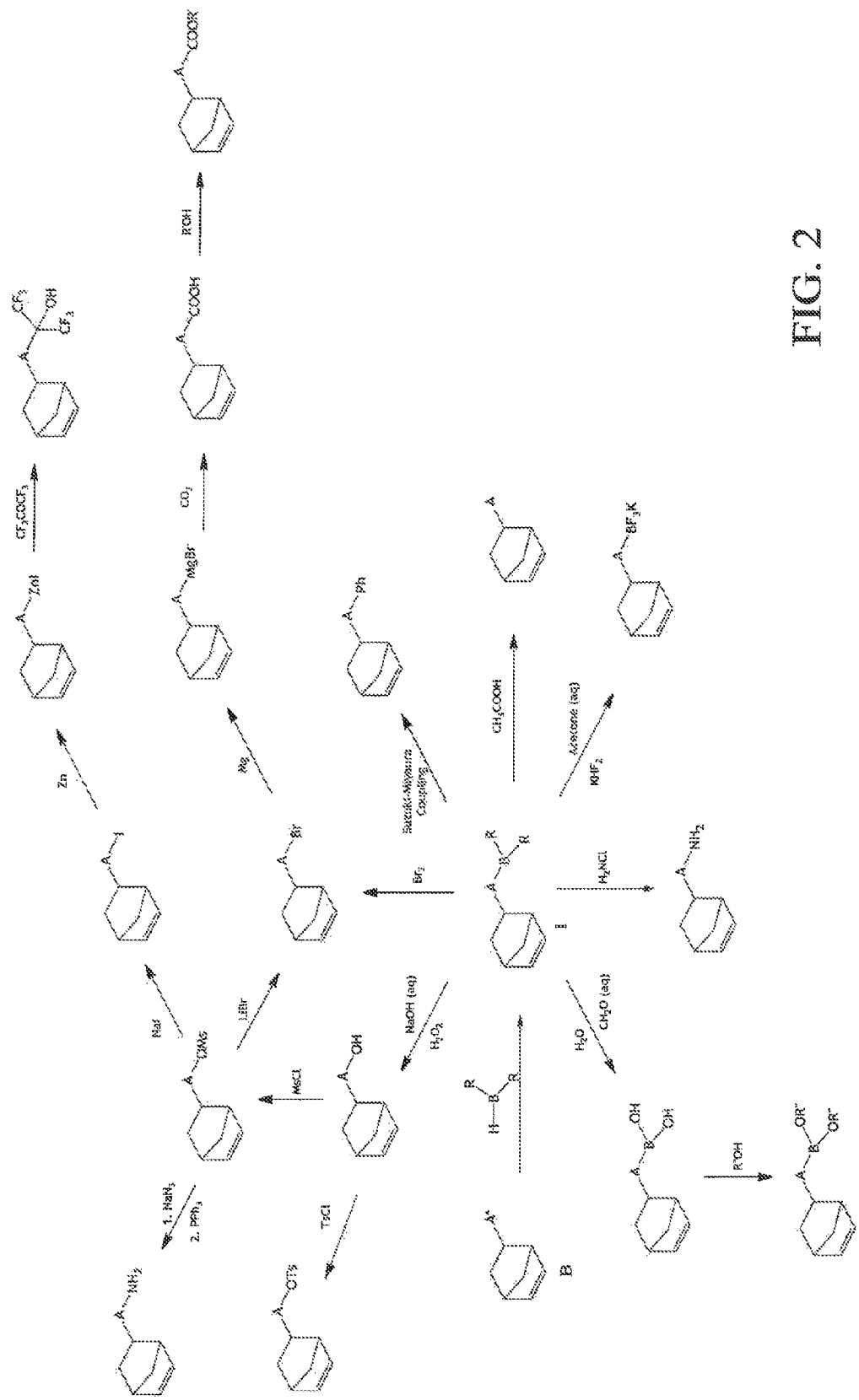
FIG. 2 is a representation of the variety of chemical transformation embodiments in accordance with the present invention.

It should also be realized that embodiments in accordance with the present invention provide means to create a wide range of functionalized norbornene-type compounds having a specific stereochemical structure in high purity. Referring now to FIG. 2, the many reactive transformations of alkenylnorbornene compound (B), through a norbornenylhydrocarbylene dihydrocarbylborane (I), to the array of functionalized norbornene-type compounds is shown therein. Advantageously, such reactive transformations do not alter the specific stereochemical structure of compound (B) thus providing a pathway to such functionalized norbornene-type materials that have high stereochemical purity that has not, until now, been available.

Thus embodiments in accordance with the present invention encompass the creation of functionalized norbornene-type compounds (or monomers) that are derived from a norbornenyl-type hydrocarbylene dihydrocarbylborane as represented by Formula (I), as well as the those represented by Formulae (II) and (III) that have been shown to be derived therefrom. Further such norbornenyl-type hydrocarbylene dihydrocarbylborane can have either an exo- or endo-configuration in high purity.

In addition, embodiments of the present invention encompass dihydrocarbylboranes, as represented by Formula (A), where the calculated C—B—C bond angle is greater than 113° for monomeric boranes, greater than 112° for dimeric boranes and greater than 106° for Lewis Base adduct boranes. Thus in all cases a 9-BBN dihydrocarbylborane is not an embodiment in accordance with the present invention. Exemplary dihydrocarbylborane embodiments of the present invention include, but are not limited to, 3,6-dimethylborepane, $Cp_2BH$, $(siamyl)_2BH$, $(3,6-Me_2Cy)_2BH$, $(2-MeCy)_2BH$, $(isopropylprenyl)_2BH$, $Cy_2BH$, di(isopinocampheyl)borane, $(3,5-Me_2Cp)_2BH$, $(mesityl)_2BH$, $(tri(isopropyl)phenyl))_2BH$ and dicyclohexylborane-2-picoline.

Further, exemplary norbornenyl-type hydrocarbylene dihydrocarbylborane embodiments in accordance with the present invention include, but are not limited to, the high stereochemical purity exo- and endo-isomers obtained by the reaction of the above, exemplary dihydrocarbylboranes, with a desired alkenylnorbornene-type compound, represented by Formula (B).

Further still, it will be realized the embodiments in accordance with the present invention are inclusive of methods to make the high regiostereochemical purity compounds of the present invention and more specifically the methods for calculating an appropriate C—B—C bond angle or an appropri-

We claim:

1. A borane compound of the Formula I:

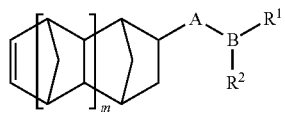

where m is 0, 1 or 2 and A is a $C_2$ to $C_{12}$ hydrocarbylene group; $R^1$ and $R^2$ are independently selected from —$CH_3$, —$C_2H_5$, a linear or branched $C_3$ to $C_{12}$ acyclic hydrocarbyl group, a substituted or unsubstituted $C_5$ to $C_7$ mono- or bicyclic hydrocarbyl group, or where $R^1$ and $R^2$ are taken together with the boron atom to which they are attached form a mono- or bicyclic structure having from 3 to 6 carbon atoms.

2. The compound of claim 1, which is selected from:
norbornenylethylbis(2,5-dimethylhex-4-en-3-yl)borane,
norbornenylbutylbis(2,5-dimethylhex-4-en-3-yl)borane,
norbornenylhexylbis(2,5-dimethylhex-4-en-3-yl)borane,
norbornenylethyldicyclohexylborane,
norbornenylbutyldicyclohexylborane,
norbornenylhexyldicyclohexylborane,
norbornenylethyldimesitylborane,
norbornenylbutyldimesitylborane and
norbornenylhexyldimesitylborane.

3. A method of forming a compound of Formula Ia:

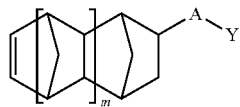

which comprises:
reacting a compound of Formula I:

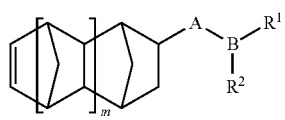

with a suitable reagent, where m is 0, 1 or 2 and A is a $C_2$ to $C_{12}$ hydrocarbylene group; $R^1$ and $R^2$ are independently selected from —$CH_3$, —$C_2H_5$, a linear or branched $C_3$ to $C_{12}$ acyclic hydrocarbyl group, a substituted or unsubstituted $C_5$ to $C_7$ mono- or bicyclic hydrocarbyl group, or where $R^1$ and $R^2$ are taken together with the boron atom to which they are attached form a mono- or bicyclic structure having from 3 to 6 carbon atoms; and
A-Y is an alkyl pendent group, an alcohol pendent group, an ether pendent group, an alkaryl pendent group, a carboxylic acid pendent group, a sulfonic acid ester pendent group or an alkyl halide pendent group.

4. The method of claim 3, where the alkaryl pendent group is —$(CH_2)_n$—Ar where n is 1 to 12 and Ar is an aromatic group.

5. The method of claim 3, where the alcohol pendent group is one of —$(CH_2)_n$—OH or —$(CH_2)_n$—$C(CF_3)_2$OH, where n is 1 to 12.

6. The method of claim 3, where the carboxylic acid pendent group is inclusive of ester derivatives and is one of —$(CH_2)_n$—C(O)OH or —$(CH_2)_n$—C(O)O$(CH_2)_m$$CH_3$, where n is 1 to 12 and m is 0 to 5.

7. The method of claim 3, where the alkyl halide pendent group is one of —$(CH_2)_n$—Br or —$(CH_2)_n$—I, where n is 1 to 12.

8. The method of claim 3, where the sulfonic acid ester pendent group is —$(CH_2)_n$—$S(O)_2$O$(CH_2)_m$$CH_3$ or —$(CH_2)_n$—$S(O)_2$O$(CH_2)_m$—Ar where n is 1 to 12, m is 0 to 5 and Ar is an aromatic group.

9. A method of making the borane compound of claim 1, comprising:
generating a dihydrocarbylborane represented by structural Formula A:

where $R^1$ and $R^2$ are independently selected from —$CH_3$, —$C_2H_5$, a linear or branched $C_3$ to $C_{12}$ acyclic hydrocarbyl group, a substituted or unsubstituted $C_5$ to $C_7$ mono- or bicyclic hydrocarbyl group, or where if $R^1$ and $R^2$ are taken together with the boron atom to which they are attached, a mono- or bicyclic structure having from 3 to 6 carbon atom, with the proviso that the C—B—C bond angle formed by the boron and the carbon of each hydrocarbyl group directly bonded to the boron have a bond angle greater than 118°;
reacting the dihydrocarbylborane and an alkenylnorbornene to generate said borane compound.

10. The method of claim 9 where the dihydrocarbylborane of structural Formula A is a dialkylborane.

11. The method of claim 10 where the dialkylborane is selected from di(cyclooctyl)borane, di(2-methylcyclopentyl)borane, dicyclopentylborane, di(3,5-dimethylcyclopentyl)borane, diisopropylprenylborane, dicyclohexylborane, di(2-methylcyclohexyl)borane, di(3,6-dimethylcyclohexyl)borane, dinorbornylborane, di(siamyl)borane, di(isopinocampheyl)borane, 3,6-dimethylborepane, di(o-tolyl)borane, dimesitylborane, (cyclohexyl)(tert-butyl)borane, (cyclohexyl)(methyl)borane, diphenylborane, or dis(2,4,6,-triisopropylphenyl).

12. The method of claim 11 where the dihydrocarbylborane is complexed with a Lewis base selected from 2-picoline, quinoline, quinoxaline, 2,3-lutidine, 2,4-lutidine, 2,5-lutidine, 5-ethyl-2-methylpyridine, 4-ethyl-2-methylpyridine, 3-ethyl-2-methylpyridine, 2,5-diethylpyridine, 5-propyl-2-methylpyridine, 4-propyl-2-methylpyridine, 5-isopropyl-2-methylpyridine, 5-t-butyl-2-methylpyridine, 5-n-hexyl-2-methylpyridine, 4-isobutyl-2-methylpyridine, and 2,4-dipropylpyridine.

13. The method of claim 9 where the dihydrocarbylborane of structural Formula A is a diarylborane.

14. The method of claim 13 where the diarylborane is selected from (o-tol)$_2$BH, $(C_6F_5)_2$BH, $(2,6-Me_2Ph)_2$BH, $(Mes)_2$BH, $(Trip)_2$BH, $(Ph)_2$BH, $(2,6-diisopropylPh)_2$BH.

15. A method for making an essentially pure exo-5-hydrocarbyl-2-norbornene monomer comprising
generating a dihydrocarbylborane selected from dicyclopentylborane, di(3,5-dimethylcyclopentyl)borane, diisopropylprenyl borane, dicyclohexylborane, di(2-methylcyclohexyl)borane, di(3,6-dimethylcyclohexyl)borane, di(siamyl)borane, di(isopinocampheyl)borane, dimesitylborane, and di(tri(isopropyl)phenyl)borane;
reacting the dihydrocarbylborane and an appropriate exo-hydrocarbylenenorbornene to generate at least one trihydrocarbylborane where the norbornenylhydrocarbylene-dihydrocarbylborane is at least 95 mol % of all trihydrocarbylboranes; and
converting the norbornenylhydrocarbylene-dihydrocarbylborane to said exo-5-hydrocarbyl-2-norbornene monomer where said monomer is at least 95 mol % of all converted trihydrocarbylboranes.

16. The method of claim 15, where the norbornenylhydrocarbylene-dihydrocarbylborane is at least 97 mol % of all trihydrocarbylboranes.

17. The method of claim 15, where the norbornenylhydrocarbylene-dihydrocarbylborane is at least 99 mol % of all trihydrocarbylboranes.

18. A method for making essentially pure endo-5-hydrocarbyl-2-norbornene monomer comprising
generating a dihydrocarbylborane selected from dicyclopentylborane, di(3,5-dimethylcyclopentyl)borane, diisopropylprenyl borane, dicyclohexylborane, di(2-methylcyclohexyl)borane, di(3,6-dimethylcyclohexyl)borane, di(siamyl)borane, di(isopinocampheyl)borane, dimesitylborane, and di(tri(isopropyl)phenyl)borane;
reacting the dihydrocarbylborane and an appropriate endo-hydrocarbylenenorbornene to generate at least one trihydrocarbylborane where the norbornenylhydrocarbylene-dihydrocarbylborane is at least 95 mol % of all trihydrocarbylboranes; and
converting the norbornenylhydrocarbylene-dihydrocarbylborane to said endo-5-hydrocarbyl-2-norbornene monomer, where said monomer is at least 95 mol % of all converted trihydrocarbylboranes.

19. The method of claim 18, where the norbornenylhydrocarbylene-dihydrocarbylborane is at least 97 mol % of all trihydrocarbylboranes.

20. The method of claim 18, where the norbornenylhydrocarbylene-dihydrocarbylborane is at least 99 mol % of all trihydrocarbylboranes.

21. A method for making essentially pure form of a compound of Formula I:

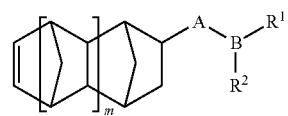

I where m is 0, 1 or 2 and A is a $C_2$ to $C_{12}$ hydrocarbylene group; $R^1$ and $R^2$ are independently selected from $-CH_3$, $-C_2H_5$, a linear or branched $C_3$ to $C_{12}$ acyclic hydrocarbyl group, a substituted or unsubstituted $C_5$ to $C_7$ mono- or bicyclic hydrocarbyl group, or where $R^1$ and $R^2$ are taken together with the boron atom to which they are attached form a mono- or bicyclic structure having from 3 to 6 carbon atoms;
which comprises,
calculating $\Delta\Delta G\ddagger$ for an organoborane of Formula A:

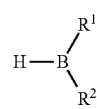

A using the equation:

$$k_{NB}/k_{vinyl} = e^{-\Delta\Delta G\ddagger/RT}$$

to predict selectivity of addition to the double bond:
where,
$k_{NB}$ is the rate constant for the addition of borane of Formula A to the internal double bond within the ring of Formula B,
$k_{vinyl}$ is the rate constant for the addition of borane of Formula A to the side chain alkenyl double bond of Formula B,
T is temperature in degree Kelvin (K),
R is ideal gas constant, and
$\Delta\Delta G\ddagger$ is the difference in free energy transition state of the borane addition to alkenyl double bond and the internal ring double bond; and
reacting said organoborane of Formula A with a compound of Formula B:

B where A* is a $C_2$ to $C_{12}$ hydrocarbyl group containing at least one C—C double bond; to form the compound of Formula (I) of purity of at least 90 percent.

* * * * *